United States Patent [19]
Li et al.

[11] Patent Number: 5,641,508
[45] Date of Patent: Jun. 24, 1997

[54] METHOD FOR DELIVERING MELANIN TO HAIR FOLLICLES

[75] Inventors: Lingna Li, La Jolla; Valeryi K. Lishko, San Diego, both of Calif.

[73] Assignee: AntiCancer, Inc., San Diego, Calif.

[21] Appl. No.: 181,471

[22] Filed: Jan. 13, 1994

[51] Int. Cl.$^6$ .............................. A61K 9/127; A61K 7/06
[52] U.S. Cl. .................. 424/450; 424/70.1; 424/70.2; 424/70.6; 514/2
[58] Field of Search ...................... 424/450, 70.1, 424/70.2, 70.6; 514/2

[56] References Cited

U.S. PATENT DOCUMENTS 3,993,436  11/1976  Fujinuma .............................. 424/70.1
5,006,331  4/1991  Gaskin .................................. 424/70.1

OTHER PUBLICATIONS

Smitz et al. *Cancer Research* 52(23) 1992 pp. 6638–6645.

*Primary Examiner*—Michael G. Wityshyn
*Assistant Examiner*—Blaine Lankford
*Attorney, Agent, or Firm*—Morrison & Foerster LLP

[57] ABSTRACT

The present invention describes a method for targeted and specific delivery of beneficial compounds, including dyes, proteins, and nucleic acids for gene therapy, to hair follicle cells using liposomes encapsulating the beneficial compound. Particularly preferred methods describe delivery of tyrosinase to the hair follicle for the purpose of improving hair color or condition, either by encapsulating the compound in liposomes, or by encapsulating a nucleic acid capable of expressing the protein in liposomes.

9 Claims, 9 Drawing Sheets

D-282

D-378

D-383

D-3886

D-3897

D-3899

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 2384 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 503..2092

( x i ) SEQUENCE DESCRIPTION: SEQ ID NO:1:

```
TATTGAGTTC   TTCAAACATT   GTAGCCTCTT   TATGGTCTCT   GAGAAATAAC   TACCTTAAAC        60

CCATAATCTT   TAATACTTCC   TAAACTTTCT   TAATAAGAGA   AGCTCTATTC   CTGACACTAC       120

CTCTCATTTG   CAAGGTCAAA   TCATCATTAG   TTTTGTAGTC   TATTAACTGG   GTTTGCTTAG       180

GTCAGGCATT   ATTATTACTA   ACCTTATTGT   TAATATTCTA   ACCATAAGAA   TTAAACTATT       240

AATGGTGAAT   AGAGTTTTTC   ACTTTAACAT   AGGCCTATCC   CACTGGTGGG   ATACGAGCCA       300

ATTCGAAAGA   AAAGTCAGTC   ATGTGCTTTT   CAGAGGATGA   AAGCTTAAGA   TAAAGACTAA       360
```

```
AAGTGTTTGA TGCTGGAGGT GGGAGTGGTA TTATATAGGT CTCAGCCAAG ACATGTGATA        420

ATCACTGTAG TAGTAGCTGG AAAGAGAAAT CTGTGACTCC AATTAGCCAG TTCCTGCAGA        480

CCTTGTGAGG ACTAGAGGAA GA ATG CTC CTG GCT GTT TTG TAC TGC CTG CTG        532
                        Met Leu Leu Ala Val Leu Tyr Cys Leu Leu
                         1               5                   10

TGG AGT TTC CAG ACC TCC GCT GGC CAT TTC CCT AGA GCC TGT GTC TCC          580
Trp Ser Phe Gln Thr Ser Ala Gly His Phe Pro Arg Ala Cys Val Ser
                15                  20                  25

TCT AAG AAC CTG ATG GAG AAG GAA TGC TGT CCA CCG TGG AGC GGG GAC          628
Ser Lys Asn Leu Met Glu Lys Glu Cys Cys Pro Pro Trp Ser Gly Asp
            30                  35                  40

AGG AGT CCC TGT GGC CAG CTT TCA GGC AGA GGT TCC TGT CAG AAT ATC          676
Arg Ser Pro Cys Gly Gln Leu Ser Gly Arg Gly Ser Cys Gln Asn Ile
        45                  50                  55

CTT CTG TCC AAT GCA CCA CTT GGG CCT CAA TTT CCC TTC ACA GGG GTG          724
Leu Leu Ser Asn Ala Pro Leu Gly Pro Gln Phe Pro Phe Thr Gly Val
    60                  65                  70

GAT GAC CGG GAG TCG TGG CCT TCC GTC TTT TAT AAT AGG ACC TGC CAG          772
Asp Asp Arg Glu Ser Trp Pro Ser Val Phe Tyr Asn Arg Thr Cys Gln
75                  80                  85                  90

TGC TCT GGC AAC TTC ATG GGA TTC AAC TGT GGA AAC TGC AAG TTT GGC          820
Cys Ser Gly Asn Phe Met Gly Phe Asn Cys Gly Asn Cys Lys Phe Gly
                95                  100                 105

TTT TGG GGA CCA AAC TGC ACA GAG AGA CGA CTC TTG GTG AGA AGA AAC          868
Phe Trp Gly Pro Asn Cys Thr Glu Arg Arg Leu Leu Val Arg Arg Asn
            110                 115                 120

ATC TTC GAT TTG AGT GCC CCA GAG AAG GAC AAA TTT TTT GCC TAC CTC          916
Ile Phe Asp Leu Ser Ala Pro Glu Lys Asp Lys Phe Phe Ala Tyr Leu
        125                 130                 135

ACT TTA GCA AAG CAT ACC ATC AGC TCA GAC TAT GTC ATC CCC ATA GGG          964
Thr Leu Ala Lys His Thr Ile Ser Ser Asp Tyr Val Ile Pro Ile Gly
    140                 145                 150

ACC TAT GGC CAA ATG AAA AAT GGA TCA ACA CCC ATG TTT AAC GAC ATC         1012
Thr Tyr Gly Gln Met Lys Asn Gly Ser Thr Pro Met Phe Asn Asp Ile
155                 160                 165                 170

AAT ATT TAT GAC CTC TTT GTC TGG ATG CAT TAT TAT GTG TCA ATG GAT         1060
Asn Ile Tyr Asp Leu Phe Val Trp Met His Tyr Tyr Val Ser Met Asp
                175                 180                 185

GCA CTG CTT GGG GGA TCT GAA ATC TGG AGA GAC ATT GAT TTT GCC CAT         1108
Ala Leu Leu Gly Gly Ser Glu Ile Trp Arg Asp Ile Asp Phe Ala His
            190                 195                 200

GAA GCA CCA GCT TTT CTG CCT TGG CAT AGA CTC TTC TTG TTG CGG TGG         1156
Glu Ala Pro Ala Phe Leu Pro Trp His Arg Leu Phe Leu Leu Arg Trp
        205                 210                 215

GAA CAA GAA ATC CAG AAG CTG ACA GGA GAT GAA AAC TTC ACT ATT CCA         1204
Glu Gln Glu Ile Gln Lys Leu Thr Gly Asp Glu Asn Phe Thr Ile Pro
    220                 225                 230

TAT TGG GAC TGG CGG GAT GCA GAA AAG TGT GAC ATT TGC ACA GAT GAG         1252
Tyr Trp Asp Trp Arg Asp Ala Glu Lys Cys Asp Ile Cys Thr Asp Glu
235                 240                 245                 250

TAC ATG GGA GGT CAG CAC CCC ACA AAT CCT AAC TTA CTC AGC CCA GCA         1300
Tyr Met Gly Gly Gln His Pro Thr Asn Pro Asn Leu Leu Ser Pro Ala
                255                 260                 265

TCA TTC TTC TCC TCT TGG CAG ATT GTC TGT AGC CGA TTG GAG GAG TAC         1348
Ser Phe Phe Ser Ser Trp Gln Ile Val Cys Ser Arg Leu Glu Glu Tyr
            270                 275                 280

AAC AGC CAT CAG TCT TTA TGC AAT GGA ACG CCC GAG GGA CCT TTA CGG         1396
Asn Ser His Gln Ser Leu Cys Asn Gly Thr Pro Glu Gly Pro Leu Arg
        285                 290                 295
```

| | | | | | | | | | | | | | | | | |
|---|---|---|---|---|---|---|---|---|---|---|---|---|---|---|---|---|
| CGT | AAT | CCT | GGA | AAC | CAT | GAC | AAA | TCC | AGA | ACC | CCA | AGG | CTC | CCC | TCT | 1444 |
| Arg | Asn | Pro | Gly | Asn | His | Asp | Lys | Ser | Arg | Thr | Pro | Arg | Leu | Pro | Ser | |
| | 300 | | | | | 305 | | | | | 310 | | | | | |
| TCA | GCT | GAT | GTA | GAA | TTT | TGC | CTG | AGT | TTG | ACC | CAA | TAT | GAA | TCT | GGT | 1492 |
| Ser | Ala | Asp | Val | Glu | Phe | Cys | Leu | Ser | Leu | Thr | Gln | Tyr | Glu | Ser | Gly | |
| 315 | | | | | 320 | | | | | 325 | | | | | 330 | |
| TCC | ATG | GAT | AAA | GCT | GCC | AAT | TTC | AGC | TTT | AGA | AAT | ACA | CTG | GAA | GGA | 1540 |
| Ser | Met | Asp | Lys | Ala | Ala | Asn | Phe | Ser | Phe | Arg | Asn | Thr | Leu | Glu | Gly | |
| | | | | 335 | | | | | 340 | | | | | 345 | | |
| TTT | GCT | AGT | CCA | CTT | ACT | GGG | ATA | GCG | GAT | GCC | TCT | CAA | AGC | AGC | ATG | 1588 |
| Phe | Ala | Ser | Pro | Leu | Thr | Gly | Ile | Ala | Asp | Ala | Ser | Gln | Ser | Ser | Met | |
| | | | 350 | | | | | 355 | | | | | 360 | | | |
| CAC | AAT | GCC | TTG | CAC | ATC | TAT | ATG | AAT | GGA | ACA | ATG | TCC | CAG | GTA | CAG | 1636 |
| His | Asn | Ala | Leu | His | Ile | Tyr | Met | Asn | Gly | Thr | Met | Ser | Gln | Val | Gln | |
| | | 365 | | | | | 370 | | | | | 375 | | | | |
| GGA | TCT | GCC | AAC | GAT | CCT | ATC | TTC | CTT | CTT | CAC | CAT | GCA | TTT | GTT | GAC | 1684 |
| Gly | Ser | Ala | Asn | Asp | Pro | Ile | Phe | Leu | Leu | His | His | Ala | Phe | Val | Asp | |
| | 380 | | | | | 385 | | | | | 390 | | | | | |
| AGT | ATT | TTT | GAG | CAG | TGG | CTC | CGA | AGG | CAC | CGT | CCT | CTT | CAA | GAA | GTT | 1732 |
| Ser | Ile | Phe | Glu | Gln | Trp | Leu | Arg | Arg | His | Arg | Pro | Leu | Gln | Glu | Val | |
| 395 | | | | | 400 | | | | | 405 | | | | | 410 | |
| TAT | CCA | GAA | GCC | AAT | GCA | CCC | ATT | GGA | CAT | AAC | CGG | GAA | TCC | TAC | ATG | 1780 |
| Tyr | Pro | Glu | Ala | Asn | Ala | Pro | Ile | Gly | His | Asn | Arg | Glu | Ser | Tyr | Met | |
| | | | | 415 | | | | | 420 | | | | | 425 | | |
| GTT | CCT | TTT | ATA | CCA | CTG | TAC | AGA | AAT | GGT | GAT | TTC | TTT | ATT | TCA | TCC | 1828 |
| Val | Pro | Phe | Ile | Pro | Leu | Tyr | Arg | Asn | Gly | Asp | Phe | Phe | Ile | Ser | Ser | |
| | | | 430 | | | | | 435 | | | | | 440 | | | |
| AAA | GAT | CTG | GGC | TAT | GAC | TAT | AGC | TAT | CTA | CAA | GAT | TCA | GAC | CCA | GAC | 1876 |
| Lys | Asp | Leu | Gly | Tyr | Asp | Tyr | Ser | Tyr | Leu | Gln | Asp | Ser | Asp | Pro | Asp | |
| | | 445 | | | | | 450 | | | | | 455 | | | | |
| TCT | TTT | CAA | GAC | TAC | ATT | AAG | TCC | TAT | TTG | GAA | CAA | GCG | AGT | CGG | ATC | 1924 |
| Ser | Phe | Gln | Asp | Tyr | Ile | Lys | Ser | Tyr | Leu | Glu | Gln | Ala | Ser | Arg | Ile | |
| | 460 | | | | | 465 | | | | | 470 | | | | | |
| TGG | TCA | TGG | CTC | CTT | GGG | GCG | GCG | ATG | GTA | GGG | GCC | GTC | CTC | ACT | GCC | 1972 |
| Trp | Ser | Trp | Leu | Leu | Gly | Ala | Ala | Met | Val | Gly | Ala | Val | Leu | Thr | Ala | |
| 475 | | | | | 480 | | | | | 485 | | | | | 490 | |
| CTG | CTG | GCA | GGG | CTT | GTG | AGC | TTG | CTG | TGT | CGT | CAC | AAG | AGA | AAG | CAG | 2020 |
| Leu | Leu | Ala | Gly | Leu | Val | Ser | Leu | Leu | Cys | Arg | His | Lys | Arg | Lys | Gln | |
| | | | | 495 | | | | | 500 | | | | | 505 | | |
| CTT | CCT | GAA | GAA | AAG | CAG | CCA | CTC | CTC | ATG | GAG | AAA | GAG | GAT | TAC | CAC | 2068 |
| Leu | Pro | Glu | Glu | Lys | Gln | Pro | Leu | Leu | Met | Glu | Lys | Glu | Asp | Tyr | His | |
| | | | 510 | | | | | 515 | | | | | 520 | | | |
| AGC | TTG | TAT | CAG | AGC | CAT | TTA | TAAAAGGCTT | AGGCAATAGA | GTAGGGCCAA | | | | | | | 2119 |
| Ser | Leu | Tyr | Gln | Ser | His | Leu | | | | | | | | | | |
| | | 525 | | | | | 530 | | | | | | | | | |

| | | | | |
|---|---|---|---|---|
| AAAGCCTGAC | CTCACTCTAA | CTCAAAGTAA | TGTCCAGGTT | CCCAGAGAAT ATCTGCTGGT | 2179 |
| ATTTTTCTGT | AAAGACCATT | TGCAAAATTG | TAACCTAATA | CAAAGTGTAG CCTTCTTCCA | 2239 |
| ACTCAGGTAG | AACACACCTG | TCTTTGTCTT | GCTGTTTCA | CTCAGCCCTT TTAACATTTT | 2299 |
| CCCCTAAGCC | CATATGTCTA | AGGAAAGGAT | GCTATTTGGT | AATGAGGAAC TGTTATTTGT | 2359 |
| ATGTGAATTA | AAGTGCTCTT | ATTTT | | | 2384 |

( 2 ) INFORMATION FOR SEQ ID NO:2:

( i ) SEQUENCE CHARACTERISTICS:
        ( A ) LENGTH: 4646 base pairs
        ( B ) TYPE: nucleic acid
        ( C ) STRANDEDNESS: single
        ( D ) TOPOLOGY: linear 5,641,508

-continued ( i i ) MOLECULE TYPE: cDNA ( i i i ) HYPOTHETICAL: NO ( i v ) ANTI-SENSE: NO ( i x ) FEATURE:
    ( A ) NAME/KEY: CDS
    ( B ) LOCATION: 425..4267

( x i ) SEQUENCE DESCRIPTION: SEQ ID NO:2:

```
CCTACTCTAT TCAGATATTC TCCAGATTCC TAAAGATTAG AGATCATTTC TCATTCTCCT        60

AGGAGTACTC ACTTCAGGAA GCAACCAGAT AAAAGAGAGG TGCAACGGAA GCCAGAACAT       120

TCCTCCTGGA AATTCAACCT GTTTCGCAGT TTCTCGAGGA ATCAGCATTC AGTCAATCCG       180

GGCCGGGAGC AGTCATCTGT GGTGAGGCTG ATTGGCTGGG CAGGAACAGC GCCGGGGCGT       240

GGGCTGAGCA CAGCGCTTCG CTCTCTTTGC CACAGGAAGC CTGAGCTCAT TCGAGTAGCG       300

GCTCTTCCAA GCTCAAAGAA GCAGAGGCCG CTGTTCGTTT CCTTTAGGTC TTTCCACTAA       360

AGTCGGAGTA TCTTCTTCCA AGATTTCACG TCTTGGTGGC CGTTCCAAGG AGCGCGAGGT       420

CGGG ATG GAT CTT GAA GGG GAC CGC AAT GGA GGA GCA AAG AAG AAG AAC       469
     Met Asp Leu Glu Gly Asp Arg Asn Gly Gly Ala Lys Lys Lys Asn
      1               5                  10                  15

TTT TTT AAA CTG AAC AAT AAA AGT GAA AAA GAT AAG AAG GAA AAG AAA       517
Phe Phe Lys Leu Asn Asn Lys Ser Glu Lys Asp Lys Lys Glu Lys Lys
             20                  25                  30

CCA ACT GTC AGT GTA TTT TCA ATG TTT CGC TAT TCA AAT TGG CTT GAC       565
Pro Thr Val Ser Val Phe Ser Met Phe Arg Tyr Ser Asn Trp Leu Asp
             35                  40                  45

AAG TTG TAT ATG GTG GTG GGA ACT TTG GCT GCC ATC ATC CAT GGG GCT       613
Lys Leu Tyr Met Val Val Gly Thr Leu Ala Ala Ile Ile His Gly Ala
             50                  55                  60

GGA CTT CCT CTC ATG ATG CTG GTG TTT GGA GAA ATG ACA GAT ATC TTT       661
Gly Leu Pro Leu Met Met Leu Val Phe Gly Glu Met Thr Asp Ile Phe
     65                  70                  75

GCA AAT GCA GGA AAT TTA GAA GAT CTG ATG TCA AAC ATC ACT AAT AGA       709
Ala Asn Ala Gly Asn Leu Glu Asp Leu Met Ser Asn Ile Thr Asn Arg
 80                  85                  90                  95

AGT GAT ATC AAT GAT ACA GGG TTC TTC ATG AAT CTG GAG GAA GAC ATG       757
Ser Asp Ile Asn Asp Thr Gly Phe Phe Met Asn Leu Glu Glu Asp Met
             100                 105                 110

ACC AGG TAT GCC TAT TAT TAC AGT GGA ATT GGT GCT GGG GTG CTG GTT       805
Thr Arg Tyr Ala Tyr Tyr Tyr Ser Gly Ile Gly Ala Gly Val Leu Val
             115                 120                 125

GCT GCT TAC ATT CAG GTT TCA TTT TGG TGC CTG GCA GCT GGA AGA CAA       853
Ala Ala Tyr Ile Gln Val Ser Phe Trp Cys Leu Ala Ala Gly Arg Gln
             130                 135                 140

ATA CAC AAA ATT AGA AAA CAG TTT TTT CAT GCT ATA ATG CGA CAG GAG       901
Ile His Lys Ile Arg Lys Gln Phe Phe His Ala Ile Met Arg Gln Glu
     145                 150                 155

ATA GGC TGG TTT GAT GTG CAC GAT GTT GGG GAG CTT AAC ACC CGA CTT       949
Ile Gly Trp Phe Asp Val His Asp Val Gly Glu Leu Asn Thr Arg Leu
160                 165                 170                 175

ACA GAT GAT GTC TCT AAG ATT AAT GAA GTT ATT GGT GAC AAA ATT GGA       997
Thr Asp Asp Val Ser Lys Ile Asn Glu Val Ile Gly Asp Lys Ile Gly
             180                 185                 190

ATG TTC TTT CAG TCA ATG GCA ACA TTT TTC ACT GGG TTT ATA GTA GGA      1045
Met Phe Phe Gln Ser Met Ala Thr Phe Phe Thr Gly Phe Ile Val Gly
             195                 200                 205

TTT ACA CGT GGT TGG AAG CTA ACC CTT GTG ATT TTG GCC ATC AGT CCT      1093
```

|     |     |     |     |     |     |     |     |     |     |     |     |     |     |     |      |
|-----|-----|-----|-----|-----|-----|-----|-----|-----|-----|-----|-----|-----|-----|-----|------|
| Phe | Thr | Arg | Gly | Trp | Lys | Leu | Thr | Leu | Val | Ile | Leu | Ala | Ile | Ser | Pro  |
|     |     | 210 |     |     |     |     | 215 |     |     |     |     | 220 |     |     |      |
| GTT | CTT | GGA | CTG | TCA | GCT | GCT | GTC | TGG | GCA | AAG | ATA | CTA | TCT | TCA | TTT  | 1141 |
| Val | Leu | Gly | Leu | Ser | Ala | Ala | Val | Trp | Ala | Lys | Ile | Leu | Ser | Ser | Phe  |
|     |     | 225 |     |     |     | 230 |     |     |     | 235 |     |     |     |     |      |
| ACT | GAT | AAA | GAA | CTC | TTA | GCG | TAT | GCA | AAA | GCT | GGA | GCA | GTA | GCT | GAA  | 1189 |
| Thr | Asp | Lys | Glu | Leu | Leu | Ala | Tyr | Ala | Lys | Ala | Gly | Ala | Val | Ala | Glu  |
| 240 |     |     |     |     | 245 |     |     |     |     | 250 |     |     |     |     | 255  |
| GAG | GTC | TTG | GCA | GCA | ATT | AGA | ACT | GTG | ATT | GCA | TTT | GGA | GGA | CAA | AAG  | 1237 |
| Glu | Val | Leu | Ala | Ala | Ile | Arg | Thr | Val | Ile | Ala | Phe | Gly | Gly | Gln | Lys  |
|     |     |     |     | 260 |     |     |     |     | 265 |     |     |     |     | 270 |      |
| AAA | GAA | CTT | GAA | AGG | TAC | AAC | AAA | AAT | TTA | GAA | GAA | GCT | AAA | AGA | ATT  | 1285 |
| Lys | Glu | Leu | Glu | Arg | Tyr | Asn | Lys | Asn | Leu | Glu | Glu | Ala | Lys | Arg | Ile  |
|     |     | 275 |     |     |     |     | 280 |     |     |     |     | 285 |     |     |      |
| GGG | ATA | AAG | AAA | GCT | ATT | ACA | GCC | AAT | ATT | TCT | ATA | GGT | GCT | GCT | TTC  | 1333 |
| Gly | Ile | Lys | Lys | Ala | Ile | Thr | Ala | Asn | Ile | Ser | Ile | Gly | Ala | Ala | Phe  |
|     |     | 290 |     |     |     |     | 295 |     |     |     |     | 300 |     |     |      |
| CTG | CTG | ATC | TAT | GCA | TCT | TAT | GCT | CTG | GCC | TTC | TGG | TAT | GGG | ACC | ACC  | 1381 |
| Leu | Leu | Ile | Tyr | Ala | Ser | Tyr | Ala | Leu | Ala | Phe | Trp | Tyr | Gly | Thr | Thr  |
|     |     | 305 |     |     |     |     | 310 |     |     |     |     | 315 |     |     |      |
| TTG | GTC | CTC | TCA | GGG | GAA | TAT | TCT | ATT | GGA | CAA | GTA | CTC | ACT | GTA | TTC  | 1429 |
| Leu | Val | Leu | Ser | Gly | Glu | Tyr | Ser | Ile | Gly | Gln | Val | Leu | Thr | Val | Phe  |
| 320 |     |     |     |     | 325 |     |     |     |     | 330 |     |     |     |     | 335  |
| TTT | TCT | GTA | TTA | ATT | GGG | GCT | TTT | AGT | GTT | GGA | CAG | GCA | TCT | CCA | AGC  | 1477 |
| Phe | Ser | Val | Leu | Ile | Gly | Ala | Phe | Ser | Val | Gly | Gln | Ala | Ser | Pro | Ser  |
|     |     |     |     | 340 |     |     |     |     | 345 |     |     |     |     | 350 |      |
| ATT | GAA | GCA | TTT | GCA | AAT | GCA | AGA | GGA | GCA | GCT | TAT | GAA | ATC | TTC | AAG  | 1525 |
| Ile | Glu | Ala | Phe | Ala | Asn | Ala | Arg | Gly | Ala | Ala | Tyr | Glu | Ile | Phe | Lys  |
|     |     |     |     | 355 |     |     |     |     | 360 |     |     |     |     | 365 |      |
| ATA | ATT | GAT | AAT | AAG | CCA | AGT | ATT | GAC | AGC | TAT | TCG | AAG | AGT | GGG | CAC  | 1573 |
| Ile | Ile | Asp | Asn | Lys | Pro | Ser | Ile | Asp | Ser | Tyr | Ser | Lys | Ser | Gly | His  |
|     |     | 370 |     |     |     |     | 375 |     |     |     |     | 380 |     |     |      |
| AAA | CCA | GAT | AAT | ATT | AAG | GGA | AAT | TTG | GAA | TTC | AGA | AAT | GTT | CAC | TTC  | 1621 |
| Lys | Pro | Asp | Asn | Ile | Lys | Gly | Asn | Leu | Glu | Phe | Arg | Asn | Val | His | Phe  |
|     | 385 |     |     |     |     | 390 |     |     |     |     | 395 |     |     |     |      |
| AGT | TAC | CCA | TCT | CGA | AAA | GAA | GTT | AAG | ATC | TTG | AAG | GGC | CTG | AAC | CTG  | 1669 |
| Ser | Tyr | Pro | Ser | Arg | Lys | Glu | Val | Lys | Ile | Leu | Lys | Gly | Leu | Asn | Leu  |
| 400 |     |     |     |     | 405 |     |     |     |     | 410 |     |     |     |     | 415  |
| AAG | GTG | CAG | AGT | GGG | CAG | ACG | GTG | GCC | CTG | GTT | GGA | AAC | AGT | GGC | TGT  | 1717 |
| Lys | Val | Gln | Ser | Gly | Gln | Thr | Val | Ala | Leu | Val | Gly | Asn | Ser | Gly | Cys  |
|     |     |     |     | 420 |     |     |     |     | 425 |     |     |     |     | 430 |      |
| GGG | AAG | AGC | ACA | ACA | GTC | CAG | CTG | ATG | CAG | AGG | CTC | TAT | GAC | CCC | ACA  | 1765 |
| Gly | Lys | Ser | Thr | Thr | Val | Gln | Leu | Met | Gln | Arg | Leu | Tyr | Asp | Pro | Thr  |
|     |     |     | 435 |     |     |     |     | 440 |     |     |     |     | 445 |     |      |
| GAG | GGG | ATG | GTC | AGT | GTT | GAT | GGA | CAG | GAT | ATT | AGG | ACC | ATA | AAT | GTA  | 1813 |
| Glu | Gly | Met | Val | Ser | Val | Asp | Gly | Gln | Asp | Ile | Arg | Thr | Ile | Asn | Val  |
|     |     |     | 450 |     |     |     |     | 455 |     |     |     |     | 460 |     |      |
| AGG | TTT | CTA | CGG | GAA | ATC | ATT | GGT | GTG | GTG | AGT | CAG | GAA | CCT | GTA | TTG  | 1861 |
| Arg | Phe | Leu | Arg | Glu | Ile | Ile | Gly | Val | Val | Ser | Gln | Glu | Pro | Val | Leu  |
|     | 465 |     |     |     |     | 470 |     |     |     |     | 475 |     |     |     |      |
| TTT | GCC | ACC | ACG | ATA | GCT | GAA | AAC | ATT | CGC | TAT | GGC | CGT | GAA | AAT | GTC  | 1909 |
| Phe | Ala | Thr | Thr | Ile | Ala | Glu | Asn | Ile | Arg | Tyr | Gly | Arg | Glu | Asn | Val  |
| 480 |     |     |     |     | 485 |     |     |     |     | 490 |     |     |     |     | 495  |
| ACC | ATG | GAT | GAG | ATT | GAG | AAA | GCT | GTC | AAG | GAA | GCC | AAT | GCC | TAT | GAC  | 1957 |
| Thr | Met | Asp | Glu | Ile | Glu | Lys | Ala | Val | Lys | Glu | Ala | Asn | Ala | Tyr | Asp  |
|     |     |     |     | 500 |     |     |     |     | 505 |     |     |     |     | 510 |      |
| TTT | ATC | ATG | AAA | CTG | CCT | CAT | AAA | TTT | GAC | ACC | CTG | GTT | GGA | GAG | AGA  | 2005 |
| Phe | Ile | Met | Lys | Leu | Pro | His | Lys | Phe | Asp | Thr | Leu | Val | Gly | Glu | Arg  |
|     |     |     | 515 |     |     |     |     | 520 |     |     |     |     | 525 |     |      |
| GGG | GCC | CAG | TTG | AGT | GGT | GGG | CAG | AAG | CAG | AGG | ATC | GCC | ATT | GCA | CGT  | 2053 |

| | | | | | | | | | | | | | | | |
|---|---|---|---|---|---|---|---|---|---|---|---|---|---|---|---|
| Gly | Ala | Gln | Leu | Ser | Gly | Gly | Gln | Lys | Gln | Arg | Ile | Ala | Ile | Ala | Arg |
| | | 530 | | | | | 535 | | | | | 540 | | | |

| GCC | CTG | GTT | CGC | AAC | CCC | AAG | ATC | CTC | CTG | CTG | GAT | GAG | GCC | ACG | TCA | 2101 |
|---|---|---|---|---|---|---|---|---|---|---|---|---|---|---|---|---|
| Ala | Leu | Val | Arg | Asn | Pro | Lys | Ile | Leu | Leu | Leu | Asp | Glu | Ala | Thr | Ser |
| | 545 | | | | | 550 | | | | | 555 | | | | |

| GCC | TTG | GAC | ACA | GAA | AGC | GAA | GCA | GTG | GTT | CAG | GTG | GCT | CTG | GAT | AAG | 2149 |
|---|---|---|---|---|---|---|---|---|---|---|---|---|---|---|---|---|
| Ala | Leu | Asp | Thr | Glu | Ser | Glu | Ala | Val | Val | Gln | Val | Ala | Leu | Asp | Lys |
| 560 | | | | | 565 | | | | | 570 | | | | | 575 |

| GCC | AGA | AAA | GGT | CGG | ACC | ACC | ATT | GTG | ATA | GCT | CAT | CGT | TTG | TCT | ACA | 2197 |
|---|---|---|---|---|---|---|---|---|---|---|---|---|---|---|---|---|
| Ala | Arg | Lys | Gly | Arg | Thr | Thr | Ile | Val | Ile | Ala | His | Arg | Leu | Ser | Thr |
| | | | | 580 | | | | | 585 | | | | | 590 | |

| GTT | CGT | AAT | GCT | GAC | GTC | ATC | GCT | GGT | TTC | GAT | GAT | GGA | GTC | ATT | GTG | 2245 |
|---|---|---|---|---|---|---|---|---|---|---|---|---|---|---|---|---|
| Val | Arg | Asn | Ala | Asp | Val | Ile | Ala | Gly | Phe | Asp | Asp | Gly | Val | Ile | Val |
| | | | 595 | | | | | 600 | | | | | 605 | | |

| GAG | AAA | GGA | AAT | CAT | GAT | GAA | CTC | ATG | AAA | GAG | AAA | GGC | ATT | TAC | TTC | 2293 |
|---|---|---|---|---|---|---|---|---|---|---|---|---|---|---|---|---|
| Glu | Lys | Gly | Asn | His | Asp | Glu | Leu | Met | Lys | Glu | Lys | Gly | Ile | Tyr | Phe |
| | | 610 | | | | | 615 | | | | | 620 | | | |

| AAA | CTT | GTC | ACA | ATG | CAG | ACA | GCA | GGA | AAT | GAA | GTT | GAA | TTA | GAA | AAT | 2341 |
|---|---|---|---|---|---|---|---|---|---|---|---|---|---|---|---|---|
| Lys | Leu | Val | Thr | Met | Gln | Thr | Ala | Gly | Asn | Glu | Val | Glu | Leu | Glu | Asn |
| | 625 | | | | | 630 | | | | | 635 | | | | |

| GCA | GCT | GAT | GAA | TCC | AAA | AGT | GAA | ATT | GAT | GCC | TTG | GAA | ATG | TCT | TCA | 2389 |
|---|---|---|---|---|---|---|---|---|---|---|---|---|---|---|---|---|
| Ala | Ala | Asp | Glu | Ser | Lys | Ser | Glu | Ile | Asp | Ala | Leu | Glu | Met | Ser | Ser |
| 640 | | | | | 645 | | | | | 650 | | | | | 655 |

| AAT | GAT | TCA | AGA | TCC | AGT | CTA | ATA | AGA | AAA | AGA | TCA | ACT | CGT | AGG | AGT | 2437 |
|---|---|---|---|---|---|---|---|---|---|---|---|---|---|---|---|---|
| Asn | Asp | Ser | Arg | Ser | Ser | Leu | Ile | Arg | Lys | Arg | Ser | Thr | Arg | Arg | Ser |
| | | | | 660 | | | | | 665 | | | | | 670 | |

| GTC | CGT | GGA | TCA | CAA | GCC | CAA | GAC | AGA | AAG | CTT | AGT | ACC | AAA | GAG | GCT | 2485 |
|---|---|---|---|---|---|---|---|---|---|---|---|---|---|---|---|---|
| Val | Arg | Gly | Ser | Gln | Ala | Gln | Asp | Arg | Lys | Leu | Ser | Thr | Lys | Glu | Ala |
| | | | 675 | | | | | 680 | | | | | 685 | | |

| CTG | GAT | GAA | AGT | ATA | CCT | CCA | GTT | TCC | TTT | TGG | AGG | ATT | ATG | AAG | CTA | 2533 |
|---|---|---|---|---|---|---|---|---|---|---|---|---|---|---|---|---|
| Leu | Asp | Glu | Ser | Ile | Pro | Pro | Val | Ser | Phe | Trp | Arg | Ile | Met | Lys | Leu |
| | | 690 | | | | | 695 | | | | | 700 | | | |

| AAT | TTA | ACT | GAA | TGG | CCT | TAT | TTT | GTT | GTT | GGT | GTA | TTT | TGT | GCC | ATT | 2581 |
|---|---|---|---|---|---|---|---|---|---|---|---|---|---|---|---|---|
| Asn | Leu | Thr | Glu | Trp | Pro | Tyr | Phe | Val | Val | Gly | Val | Phe | Cys | Ala | Ile |
| | 705 | | | | | 710 | | | | | 715 | | | | |

| ATA | AAT | GGA | GGC | CTG | CAA | CCA | GCA | TTT | GCA | ATA | ATA | TTT | TCA | AAG | ATT | 2629 |
|---|---|---|---|---|---|---|---|---|---|---|---|---|---|---|---|---|
| Ile | Asn | Gly | Gly | Leu | Gln | Pro | Ala | Phe | Ala | Ile | Ile | Phe | Ser | Lys | Ile |
| 720 | | | | | 725 | | | | | 730 | | | | | 735 |

| ATA | GGG | GTT | TTT | ACA | AGA | ATT | GAT | GAT | CCT | GAA | ACA | AAA | CGA | CAG | AAT | 2677 |
|---|---|---|---|---|---|---|---|---|---|---|---|---|---|---|---|---|
| Ile | Gly | Val | Phe | Thr | Arg | Ile | Asp | Asp | Pro | Glu | Thr | Lys | Arg | Gln | Asn |
| | | | | 740 | | | | | 745 | | | | | 750 | |

| AGT | AAC | TTG | TTT | TCA | CTA | TTG | TTT | CTA | GCC | CTT | GGA | ATT | ATT | TCT | TTT | 2725 |
|---|---|---|---|---|---|---|---|---|---|---|---|---|---|---|---|---|
| Ser | Asn | Leu | Phe | Ser | Leu | Leu | Phe | Leu | Ala | Leu | Gly | Ile | Ile | Ser | Phe |
| | | | 755 | | | | | 760 | | | | | 765 | | |

| ATT | ACA | TTT | TTC | CTT | CAG | GGT | TTC | ACA | TTT | GGC | AAA | GCT | GGA | GAG | ATC | 2773 |
|---|---|---|---|---|---|---|---|---|---|---|---|---|---|---|---|---|
| Ile | Thr | Phe | Phe | Leu | Gln | Gly | Phe | Thr | Phe | Gly | Lys | Ala | Gly | Glu | Ile |
| | | 770 | | | | | 775 | | | | | 780 | | | |

| CTC | ACC | AAG | CGG | CTC | CGA | TAC | ATG | GTT | TTC | CGA | TCC | ATG | CTC | AGA | CAG | 2821 |
|---|---|---|---|---|---|---|---|---|---|---|---|---|---|---|---|---|
| Leu | Thr | Lys | Arg | Leu | Arg | Tyr | Met | Val | Phe | Arg | Ser | Met | Leu | Arg | Gln |
| | 785 | | | | | 790 | | | | | 795 | | | | |

| GAT | GTG | AGT | TGG | TTT | GAT | GAC | CCT | AAA | AAC | ACC | ACT | GGA | GCA | TTG | ACT | 2869 |
|---|---|---|---|---|---|---|---|---|---|---|---|---|---|---|---|---|
| Asp | Val | Ser | Trp | Phe | Asp | Asp | Pro | Lys | Asn | Thr | Thr | Gly | Ala | Leu | Thr |
| 800 | | | | | 805 | | | | | 810 | | | | | 815 |

| ACC | AGG | CTC | GCC | AAT | GAT | GCT | GCT | CAA | GTT | AAA | GGG | GCT | ATA | GGT | TCC | 2917 |
|---|---|---|---|---|---|---|---|---|---|---|---|---|---|---|---|---|
| Thr | Arg | Leu | Ala | Asn | Asp | Ala | Ala | Gln | Val | Lys | Gly | Ala | Ile | Gly | Ser |
| | | | | 820 | | | | | 825 | | | | | 830 | |

| AGG | CTT | GCT | GTA | ATT | ACC | CAG | AAT | ATA | GCA | AAT | CTT | GGG | ACA | GGA | ATA | 2965 |
|---|---|---|---|---|---|---|---|---|---|---|---|---|---|---|---|---|
| Arg | Leu | Ala | Val | Ile | Thr | Gln | Asn | Ile | Ala | Asn | Leu | Gly | Thr | Gly | Ile |
| | | | | 835 | | | | | 840 | | | | | 845 | |

| ATT | ATA | TCC | TTC | ATC | TAT | GGT | TGG | CAA | CTA | ACA | CTG | TTA | CTC | TTA | GCA | 3013 |

```
Ile Ile Ser Phe Ile Tyr Gly Trp Gln Leu Thr Leu Leu Leu Ala
    850                 855                 860

ATT GTA CCC ATC ATT GCA ATA GCA GGA GTT GTT GAA ATG AAA ATG TTG          3061
Ile Val Pro Ile Ile Ala Ile Ala Gly Val Val Glu Met Lys Met Leu
        865                 870                 875

TCT GGA CAA GCA CTG AAA GAT AAG AAA GAA CTA GAA GGT GCT GGG AAG          3109
Ser Gly Gln Ala Leu Lys Asp Lys Lys Glu Leu Glu Gly Ala Gly Lys
880                 885                 890                 895

ATC GCT ACT GAA GCA ATA GAA AAC TTC CGA ACC GTT GTT TCT TTG ACT          3157
Ile Ala Thr Glu Ala Ile Glu Asn Phe Arg Thr Val Val Ser Leu Thr
            900                 905                 910

CAG GAG CAG AAG TTT GAA CAT ATG TAT GCT CAG AGT TTG CAG GTA CCA          3205
Gln Glu Gln Lys Phe Glu His Met Tyr Ala Gln Ser Leu Gln Val Pro
                915                 920                 925

TAC AGA AAC TCT TTG AGG AAA GCA CAC ATC TTT GGA ATT ACA TTT TCC          3253
Tyr Arg Asn Ser Leu Arg Lys Ala His Ile Phe Gly Ile Thr Phe Ser
            930                 935                 940

TTC ACC CAG GCA ATG ATG TAT TTT TCC TAT GCT GGA TGT TTC CGG TTT          3301
Phe Thr Gln Ala Met Met Tyr Phe Ser Tyr Ala Gly Cys Phe Arg Phe
        945                 950                 955

GGA GCC TAC TTG GTG GCA CAT AAA CTC ATG AGC TTT GAG GAT GTT CTG          3349
Gly Ala Tyr Leu Val Ala His Lys Leu Met Ser Phe Glu Asp Val Leu
960                 965                 970                 975

TTA GTA TTT TCA GCT GTT GTC TTT GGT GCC ATG GCC GTG GGG CAA GTC          3397
Leu Val Phe Ser Ala Val Val Phe Gly Ala Met Ala Val Gly Gln Val
            980                 985                 990

AGT TCA TTT GCT CCT GAC TAT GCC AAA GCC AAA ATA TCA GCA GCC CAC          3445
Ser Ser Phe Ala Pro Asp Tyr Ala Lys Ala Lys Ile Ser Ala Ala His
                995                 1000                1005

ATC ATC ATG ATC ATT GAA AAA ACC CCT TTG ATT GAC AGC TAC AGC ACG          3493
Ile Ile Met Ile Ile Glu Lys Thr Pro Leu Ile Asp Ser Tyr Ser Thr
            1010                1015                1020

GAA GGC CTA ATG CCG AAC ACA TTG GAA GGA AAT GTC ACA TTT GGT GAA          3541
Glu Gly Leu Met Pro Asn Thr Leu Glu Gly Asn Val Thr Phe Gly Glu
        1025                1030                1035

GTT GTA TTC AAC TAT CCC ACC CGA CCG GAC ATC CCA GTG CTT CAG GGA          3589
Val Val Phe Asn Tyr Pro Thr Arg Pro Asp Ile Pro Val Leu Gln Gly
1040                1045                1050                1055

CTG AGC CTG GAG GTG AAG AAG GGC CAG ACG CTG GCT CTG GTG GGC AGC          3637
Leu Ser Leu Glu Val Lys Lys Gly Gln Thr Leu Ala Leu Val Gly Ser
            1060                1065                1070

AGT GGC TGT GGG AAG AGC ACA GTG GTC CAG CTC CTG GAG CGG TTC TAC          3685
Ser Gly Cys Gly Lys Ser Thr Val Val Gln Leu Leu Glu Arg Phe Tyr
        1075                1080                1085

GAC CCC TTG GCA GGG AAA GTG CTG CTT GAT GGC AAA GAA ATA AAG CGA          3733
Asp Pro Leu Ala Gly Lys Val Leu Leu Asp Gly Lys Glu Ile Lys Arg
    1090                1095                1100

CTG AAT GTT CAG TGG CTC CGA GCA CAC CTG GGC ATC GTG TCC CAG GAG          3781
Leu Asn Val Gln Trp Leu Arg Ala His Leu Gly Ile Val Ser Gln Glu
1105                1110                1115

CCC ATC CTG TTT GAC TGC AGC ATT GCT GAG AAC ATT GCC TAT GGA GAC          3829
Pro Ile Leu Phe Asp Cys Ser Ile Ala Glu Asn Ile Ala Tyr Gly Asp
1120                1125                1130                1135

AAC AGC CGG GTG GTG TCA CAG GAA GAG ATC GTG AGG GCA GCA AAG GAG          3877
Asn Ser Arg Val Val Ser Gln Glu Glu Ile Val Arg Ala Ala Lys Glu
            1140                1145                1150

GCC AAC ATA CAT GCC TTC ATC GAG TCA CTG CCT AAT AAA TAT AGC ACT          3925
Ala Asn Ile His Ala Phe Ile Glu Ser Leu Pro Asn Lys Tyr Ser Thr
        1155                1160                1165

AAA GTA GGA GAC AAA GGA ACT CAG CTC TCT GGT GGC CAG AAA CAA CGC          3973
```

| | | | | | | | | | | | | | | | | |
|---|---|---|---|---|---|---|---|---|---|---|---|---|---|---|---|---|
| Lys | Val | Gly | Asp | Lys | Gly | Thr | Gln | Leu | Ser | Gly | Gly | Gln | Lys | Gln | Arg | |
| | | 1170 | | | | 1175 | | | | | 1180 | | | | | |

```
ATT  GCC  ATA  GCT  CGT  GCC  CTT  GTT  AGA  CAG  CCT  CAT  ATT  TTG  CTT  TTG          4021
Ile  Ala  Ile  Ala  Arg  Ala  Leu  Val  Arg  Gln  Pro  His  Ile  Leu  Leu  Leu
         1185                    1190                    1195

GAT  GAA  GCC  ACG  TCA  GCT  CTG  GAT  ACA  GAA  AGT  GAA  AAG  GTT  GTC  CAA          4069
Asp  Glu  Ala  Thr  Ser  Ala  Leu  Asp  Thr  Glu  Ser  Glu  Lys  Val  Val  Gln
1200                    1205                    1210                    1215

GAA  GCC  CTG  GAC  AAA  GCC  AGA  GAA  GGC  CGC  ACC  TGC  ATT  GTG  ATT  GCT          4117
Glu  Ala  Leu  Asp  Lys  Ala  Arg  Glu  Gly  Arg  Thr  Cys  Ile  Val  Ile  Ala
                   1220                    1225                    1230

CAC  CGC  CTG  TCC  ACC  ATC  CAG  AAT  GCA  GAC  TTA  ATA  GTG  GTG  TTT  CAG          4165
His  Arg  Leu  Ser  Thr  Ile  Gln  Asn  Ala  Asp  Leu  Ile  Val  Val  Phe  Gln
              1235                    1240                    1245

AAT  GGC  AGA  GTC  AAG  GAG  CAT  GGC  ACG  CAT  CAG  CAG  CTG  CTG  GCA  CAG          4213
Asn  Gly  Arg  Val  Lys  Glu  His  Gly  Thr  His  Gln  Gln  Leu  Leu  Ala  Gln
         1250                    1255                    1260

AAA  GGC  ATC  TAT  TTT  TCA  ATG  GTC  AGT  GTC  CAG  GCT  GGA  ACA  AAG  CGC          4261
Lys  Gly  Ile  Tyr  Phe  Ser  Met  Val  Ser  Val  Gln  Ala  Gly  Thr  Lys  Arg
    1265                    1270                    1275

CAG  TGAACTCTGA CTGTATGAGA TGTTAAATAC TTTTAATAT TTGTTTAGAT                               4314
Gln

1280

ATGACATTTA  TTCAAAGTTA  AAAGCAAACA  CTTACAGAAT  TATGAAGAGG  TATCTGTTTA                   4374

ACATTTCCTC  AGTCAAGTTC  AGAGTCTTCA  GAGACTTCGT  AATTAAAGGA  ACAGAGTGAG                   4434

AGACATCATC  AAGTGGAGAG  AAATCATAGT  TTAAACTGCA  TTATAAATTT  TATAACAGAA                   4494

TTAAAGTAGA  TTTTAAAGA   TAAAATGTGT  AATTTTGTTT  ATATTTCCC   ATTTGGACTG                   4554

TAACTGACTG  CCTTGCTAAA  AGATTATAGA  AGTAGCAAAA  AGTATTGAAA  TGTTTGCATA                   4614

AAGTGTCTAT  AATAAAACTA  AACTTTCATG  TG                                                  4646
```

( 2 ) INFORMATION FOR SEQ ID NO:3:

( i ) SEQUENCE CHARACTERISTICS:
        ( A ) LENGTH: 867 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 35..517

( x i ) SEQUENCE DESCRIPTION: SEQ ID NO:3:

```
AGGCTGGAGA  GCCTGCTGCC  CGCCCGCCCG  TAAA ATG GTC CCC TCG GCT GGA                          52
                                         Met Val Pro Ser Ala Gly
                                         1               5

CAG  CTC  GCC  CTG  TTC  GCT  CTG  GGT  ATT  GTG  TTG  GCT  GCG  TGC  CAG  GCC          100
Gln  Leu  Ala  Leu  Phe  Ala  Leu  Gly  Ile  Val  Leu  Ala  Ala  Cys  Gln  Ala
              10                      15                      20

TTG  GAG  AAC  AGC  ACG  TCC  CCG  CTG  AGT  GCA  GAC  CCG  CCC  GTG  GCT  GCA          148
Leu  Glu  Asn  Ser  Thr  Ser  Pro  Leu  Ser  Ala  Asp  Pro  Pro  Val  Ala  Ala
         25                      30                      35

GCA  GTG  GTG  TCC  CAT  TTT  AAT  GAC  TGC  CCA  GAT  TCC  CAC  ACT  CAG  TTC          196
Ala  Val  Val  Ser  His  Phe  Asn  Asp  Cys  Pro  Asp  Ser  His  Thr  Gln  Phe
```

-continued

| | | | | | | | | | | | | | | | | |
|---|---|---|---|---|---|---|---|---|---|---|---|---|---|---|---|---|
| | | | 40 | | | | 45 | | | | | 50 | | | | |
| TGC | TTC | CAT | GCA | ACC | TGC | AGG | TTT | TTG | GTG | CAC | GAG | GAC | AAG | CCA | GCA | 244 |
| Cys | Phe | His | Ala | Thr | Cys | Arg | Phe | Leu | Val | His | Glu | Asp | Lys | Pro | Ala | |
| 55 | | | | | 60 | | | | | 65 | | | | | 70 | |
| TGT | GTC | TGC | CAT | TCT | GGG | TAC | GTT | GGT | GCA | CGC | TGT | GAG | CAT | GCG | GAC | 292 |
| Cys | Val | Cys | His | Ser | Gly | Tyr | Val | Gly | Ala | Arg | Cys | Glu | His | Ala | Asp | |
| | | | | 75 | | | | | 80 | | | | | 85 | | |
| CTC | CTG | GCC | GTG | GTG | GCT | GCC | AGC | CAG | AAG | AAG | CAG | GCC | ATC | ACC | GCC | 340 |
| Leu | Leu | Ala | Val | Val | Ala | Ala | Ser | Gln | Lys | Lys | Gln | Ala | Ile | Thr | Ala | |
| | | | 90 | | | | | 95 | | | | | 100 | | | |
| TTG | GTG | GTG | GTC | TCC | ATC | GTG | GCC | CTG | GCT | GTC | CTT | ATC | ATC | ACA | TGT | 388 |
| Leu | Val | Val | Val | Ser | Ile | Val | Ala | Leu | Ala | Val | Leu | Ile | Ile | Thr | Cys | |
| | | 105 | | | | | 110 | | | | | 115 | | | | |
| GTG | CTG | ATA | CAC | TGC | TGC | CAG | GTC | CGA | AAA | CAC | TGT | GAG | TGG | TGC | CGG | 436 |
| Val | Leu | Ile | His | Cys | Cys | Gln | Val | Arg | Lys | His | Cys | Glu | Trp | Cys | Arg | |
| | 120 | | | | | 125 | | | | | 130 | | | | | |
| GCC | CTC | ATC | TGC | CGG | CAC | GAG | AAG | CCC | AGC | GCC | CTC | CTG | AAG | GGA | AGA | 484 |
| Ala | Leu | Ile | Cys | Arg | His | Glu | Lys | Pro | Ser | Ala | Leu | Leu | Lys | Gly | Arg | |
| 135 | | | | | 140 | | | | | 145 | | | | | 150 | |
| ACC | GCT | TGC | TGC | CAC | TCA | GAA | ACA | CTC | GTC | TGAAGAGCCC | | AGAGGAGGAG | | | | 534 |
| Thr | Ala | Cys | Cys | His | Ser | Glu | Thr | Leu | Val | | | | | | | |
| | | | | 155 | | | | | 160 | | | | | | | |

| | | | | |
|---|---|---|---|---|
| TTTGGCCAGG | TGGACTGTGG | CAGATCAATA | AAGAAAGGCT | TCTTCAGGAC | AGCACTGCCA | 594 |
| GAGATGCCTG | GGTGTGCCAC | AGACCTTCCT | ACTTGGCCTG | TAATCACCTG | TGCAGCCTTT | 654 |
| TGTGGGCCTT | CAAAACTCTG | TCAAGAACTC | CGTCGGCTTG | GGGTTATTCA | GTGTGACCTA | 714 |
| GAGAAGAAAT | CAGCGGACCA | CGATTTCAAG | ACTTGTTAAA | AAAGAACTGC | AAAGAGACGG | 774 |
| ACTCCTGTTC | ACCTAGGTGA | GGTGTGTGCA | GCAGTTGGTG | TCTGAGTCCA | CATGTGTGCA | 834 |
| GTTGTCTTCT | GCCAGCCATG | GATTCCAGGC | CGT | | | 867 |

METHOD FOR DELIVERING MELANIN TO HAIR FOLLICLES

CROSS-REFERENCE TO RELATED APPLICATIONS

This application is related to copending application Ser. No. 08/041,553, filed Apr. 2, 1993, the disclosures of which are hereby incorporated by reference.

TECHNICAL FIELD OF THE INVENTION

This invention relates to methods for specifically delivering therapeutic or other beneficial compounds to hair follicles to improve hair growing from the follicles.

BACKGROUND OF THE INVENTION

There has been a long-felt need for methods of directly influencing hair growth, color and appearance, especially for treatment of alopecia in humans.

Surgical transplantation of small, discrete, skin areas having viable follicles to areas having inactive follicles is expensive, labor-intensive and relatively short-lasting. Also, as described by R. F. Oliver et al. in U.S. Pat. No. 4,919,664, follicular dermal cells can be inserted into a skin incision, resulting in hair growth along the incision. However, this is a complex technique that does nothing to stimulate existing follicles.

Treatment of the hair and skin with various creams or lotions with biologically active ingredients to improve hair growth and other conditions has generally low efficiency. A wide variety of externally applied agents are available for application to the hair to improve body, flexibility, curl, etc. are available. These have limited and only short term usefulness. Coloring hair with various dyes requires frequent repetitions and is not always natural in appearance.

The use of biologically active compounds that are hair growth stimulators or advantageously change other hair characteristics, such as color, would seem to be a more natural and attractive approach, especially at the stage where hair-follicle cells still exist but hair growth, for unknown reasons, is adversely affected. Attempts to follow this approach have been ineffective, possibly because of the inability of stimulators to penetrate the cellular membrane of hair follicle cells and to enter into the cells where their action is needed.

In the treatment of skin with various absorbable lotions and the like it has long been known that absorption is generally greater in skin areas of higher follicular density. See, for example, Maigach et al, *Arch. Environ. Health*, 23:208–211 (1971). The absorbed materials, however, were entirely different from liposomes. It was not appreciated prior to the present invention that liposomes could be used to direct beneficial compositions preferentially to hair follicles.

Liposomes, which are artificial phospholipid vesicles, have been successfully used for delivery of different low-molecular-weight water-soluble and oil-soluble compounds into different cells. See, for example, G. Gregoriadis, *Trends in Biotechnology*, 3:235–241 (1985) and K. H. Schmidt, ed., Liposomes as drug carriers, Stuttgart: George Thieme Verlag (1986).

Liposomes are typically formed by mixing dry phospholipids with aqueous solutions giving rise to bilayers of phospholipid molecules which arrange themselves spontaneously to form close multilayered spherules. As they form, the liposomes entrap liquid and any soluble solutes that are present. A large number of substances that do not interfere with the formation of the liposomes can be incorporated, regardless of solubility, electrical charge, size and other structural characteristics. These characteristics may, however, have adverse affects in some environments limiting the use of liposomes.

Liposomes containing antibody molecules attached for specific targeting have been described for delivery of encapsulated material to targeted cells containing an antigen immunoreactive with the attached antibody, and are referred to as immunoliposomes. See, for example, U.S. Pat. Nos. 4,755,388, 4,925,661 and 4,957,735 for descriptions of immunoliposomes. In addition, liposome compositions have been described that contain protein which are administered to mammalian skin and shown to penetrate in skin keratinocytes. See, U.S. Pat. No. 5,190,762. Furthermore, DNA-liposome compositions have also been described, but were not shown to selectively deliver the nucleic acid contents to hair follicles through topical administration. See, U.S. Pat. Nos. 5,077,211 and 5,223,263, and Hoffman et al., *FEBS Letts.*, 93:365–368 (1978).

Although various targeting mechanisms have been attempted to increase the specificity of delivery via liposomes, delivery of the encapsulated material into a targeted cell or tissue may not necessarily follow.

Specific tissue delivery is particularly important where the agent being delivered may have a deleterious effect to tissues adjacent to the targeted tissue of interest upon administration of the agent. For example, the agent may produce effects which are acceptable in the hair follicle, but not desired in the adjacent skin tissue. For example, delivery of melanin is desirable for hair pigmentation, but not for general skin pigmentation, and therefore general delivery to all surface skin cells is undesirable, requiring follicle cell specificity. Similarly, gene replacement therapy for expressing melanin or tyrosinase is undesirable in skin cells, but is a desirable result for hair pigmentation.

Transdermal drug delivery provides additional problems where the drug being delivered is destined for the circulation rather than cells of the dermis. Methods for transdermal drug delivery which minimize adsorption into cells of the skin and simultaneously increase transport to the circulation are desirable in certain instances. However, in instances where delivery is directed solely to the hair follicle, it is desirable that there is minimum adsorption into the skin and minimum transport of the compound into the systemic circulation where the administered compound can exert undesirable side effects.

A small molecule dye, carboxyfluorescein has been found to be preferentially delivered to the pilosebaceous units of hamster ear membrane when incorporated in a particular liposomal formulation, as described in a very recent paper by Lieb et al, *The Journal of Investigative Dermatology*, 99:108–113 (1992).

The prior research, however, does not describe methods of specifically targeting hair follicles with liposomes carrying large molecule agents such as proteins or nucleic acids that selectively deliver these beneficial agents to the hair follicle. Furthermore, there have not been any descriptions of methods for accurately testing in vitro the extent to which particular compounds are delivered to hair follicle cells and the effectiveness of the compounds delivered.

Thus, there is a continuing need for improved methods of delivering specific beneficial compounds to hair follicles, and for measuring effectiveness of the delivery.

SUMMARY OF THE INVENTION

It has now been discovered that liposomes can selectively target the hair follicle with potentially beneficial compounds. Basically, this method comprises preparing liposomes, incorporating beneficial compounds into the liposomes either during formation of the liposomes or thereafter, and applying the liposomes to the skin areas requiring treatment in patients requiring such beneficial treatment. According to the present methods, liposomes preferentially deliver the beneficial compounds to the hair follicles where the compounds enter into the follicle cells.

Typically, the present methods are practiced on the skin of a mammal requiring treatment according to the present methods, such as a human. Thus, the methods can be practiced in vivo.

In order to determine the effectiveness of the hair follicle-specific treatment method of the present invention, an in vitro method of testing particular liposome agents has been developed, utilizing novel histoculturing techniques.

As mentioned above, it is known that a number of compounds, typically dyes and the like, when applied to the skin are more rapidly absorbed in heavily follicularized areas. However, many macromolecular substances cannot cross the plasma membrane into the follicle cells. It has been discovered that when incorporated into liposomes, those macromolecular compounds are successfully transported into the follicle cells, and furthermore can be selectively transferred across the stratum corneum into the follicle without entry to the circulation or the adjacent skin tissue, which has great potential efficacy as well as safety advantages.

Thus, the invention describes a method of directly and selectively delivering a beneficial compound to hair follicles comprising the steps of:

a) incorporating an effective amount of at least one selected beneficial compound into a liposome; and b) applying the liposomes to skin areas having a plurality of hair follicles;

whereby the beneficial compound is preferentially transmitted to the hair follicles and enters into the hair follicles. In preferred embodiments, the beneficial compound is a protein, and more preferably is tyrosinase or hair growth stimulators such as cyclosporin-A or related compounds. In a related embodiment, the beneficial compound is a nucleic acid capable of expressing an effective amount of a replacement therapy protein. Particularly preferred are nucleic acid molecules capable of expressing tyrosinase or hair-growth stimulating proteins or the multi-drug resistance proteins conferring resistance to chemotherapy-induced alopecia.

Further contemplated are methods for restoring hair color using liposome compositions that contain tyrosinase proteins or nucleic acids capable of expressing tyrosinase.

In other embodiments, the invention contemplates the use of the present liposome compositions according to the present methods for inhibiting chemotherapy-induced alopecia. The liposome compositions contain compounds which reduce in the hair follicle the toxicity of the chemotherapy treatment.

Also contemplated are liposome compositions for use in the present methods.

BRIEF DESCRIPTION OF THE DRAWINGS

Details of the invention, and of certain preferred embodiments thereof, will be further understood upon reference to the drawing, wherein:

FIGS. 5A–5D contain light-microscopy images (magnification 125×, FIGS. 5A and 5C; magnification 250×, FIGS. 5B and 5D) of sections of skin histoculture prepared as described in Example 4b, in which FIGS. 5A and 5B illustrate results using liposome-entrapped plasmid (pM-MuLV-SV-Lac-Z) capable of expressing Lac-Z, and FIGS. 5C and 5D illustrate results using naked plasmid. The arrows indicate uniform distributions of blue (dark) spots in the hair follicles and shafts indicating active gene transfer to the hair follicles;

FIGS. 6A–6C contain fluorescent light microscopy images (magnification 150×) of sections of mouse skin samples prepared by treatment of mouse skin in vivo as described in Example 5, in which FIGS. 6A and 6B illustrate results using liposome-entrapped calcein and FIG. 6C illustrates results using naked calcein. The arrows indicate fluorescence in the hair shafts indicating active transfer of calcein to the hair follicles; and FIGS. 7A–7C contain light microscopy images (magnification 500×) of sections of mouse skin samples prepared by treatment of mouse skin in vivo as described in Example 5, in which FIGS. 7A–7C illustrate results using liposome-entrapped melanin.

DETAILED DESCRIPTION OF THE INVENTION

Figure 1A:
FIG. 1A is a fluorescent microscopy image (magnification 500×) of a skin histoculture treated with liposomes containing calcein as described in Example 1 showing highly preferential dye delivery into hair follicles.

A. Liposome-Mediated Targeted Delivery of Macromolecules and Nucleic Acids to Hair Follicles The invention relates to the administration of active compositions directly and selectively (specifically) to the cells of the hair follicle and to the hair shaft itself.

Because of the hair follicle specificity for delivery according to the present invention, the present invention provides the advantage of specifically delivering beneficial compositions to the hair follicle rather than generally to the dermis or circulation, thereby allowing the use of lower amounts of the composition to achieve the desired effect, and thereby reducing the likelihood of undesirable effects caused by the composition on the skin generally of to the general circulation.

1. Skin Histoculture Assay

In order to demonstrate that liposomes encapsulating beneficial compound are effective at selective delivery, and to provide a means for optimizing liposome mediated delivery formulations, an in vitro assay has been developed. Basically, pieces of skin containing hair follicles are histocultured on collagen-gel-supported sponges as described by Li et al, *Proc. Natl. Acad. Sci. USA*, 88:1908–1912 (1991); Li et al, *Proc. Natl. Acad. Sci. USA*, 89:8764–8768 (1992); Li et al., *In Vitro Cell. Dev. Biol.*, 28A:479–481 (1992); Li et al., *In Vitro Cell. Dev. Biol.*, 28A:679–681 (1992); Li et al., *In Vitro Cell. Dev. Biol.*, 28A:695–698 (1992); Li et al., *In Vitro Cell. Dev. Biol.*, 29A:192–194 (1993); and Li et al., *In Vitro Cell. Dev. Biol.*, 29A:449–450 (1993), the teachings of which are hereby incorporated by reference. The system allows the growth of hair shafts in the follicle cells for periods of at least 10–16 days, and further allows the ability to evaluate the three-dimensional appearance of the hair follicle and surrounding tissue by the use of selective dyes and stains in confocal microscopy, thereby providing a system for evaluating the effectiveness of the therapeutic reagent being applied. The use of the three-dimensional histoculture in conjunction with confocal microscopy allows the ability to follow the fine details of candidate beneficial (therapeutic) product-delivering liposome interactions with hair-follicles at the cellular and subcellular level. Therefore, the histoculture system allows the ability to optimize liposome compositions as well as determine the optimum conditions for delivery of the liposome contents into the target cell.

Typical skin histoculture preparation methods are also detailed in copending U.S. patent application of Li et al., Ser. No. 07/662,239, filed Feb. 28, 1992, and assigned to the assignee of this application, the teachings of which are hereby incorporated by reference.

Native-state histoculturing of a skin sample having hair follicles and internal and external surfaces comprises placing the skin sample on an extracellular support matrix immersed in a medium whereby the internal surface is adjacent to the matrix and the external surface is exposed in the air above the surface of the medium and maintaining the matrix with the skin thereon under skin culturing conditions.

Potentially any skin from any animal can be used in this assay. Preferably, the animal is a mammal. Exemplary mammals are mice, rats, guinea pigs, hamsters, rabbits, marmosets, monkeys and humans. More preferably, the animal is a human.

The skin sample having dermal and epidermal layers is typically excised from an animal. Excess fat, if present, is removed. The sample of skin may be excised from a hairy animal whose skin is capable of supporting hair growth or from a hairless animal whose skin is devoid of hair, such as an athymic, nude animal. Where the skin sample is obtained from a hairy animal, the skin may be shaved or clipped prior to excision.

The skin sample is defined herein as having internal and external surfaces. The phrase "internal surface" refers to the dermally-oriented surface; i.e. the non-exposed surface of the skin as it exists in its native-state in the animal. The phrase "external surface" refers to the epidermally-oriented surface: i.e. the exposed surface of the skin as it exists in its native-state in the animal.

There is no real limitation as to the surface area of a piece of skin used in the present invention. Typically, the skin sample can range in external surface area from about 1 to about 10,000 square millimeters ($mm^2$). A preferred surface area is from about 4 to about 100 $mm^2$. A more preferred surface area is about 10 $mm^2$. The thickness of the skin is a function of the animal from which it is obtained. Where the skin sample is excised from a mouse, a preferred thickness is about 1 to 2 mm.

Skin samples are cultured on a support matrix. A support matrix of this invention provides a trabecular structure with interstices suited for capillary action to deliver aqueous nutrients from the medium to the internal surface (base) the skin as in a native state. Thus, any support having this capacity is contemplated including synthetic meshes such as nylon, borosilicate glass fiber, or polypropylene or organic meshes such as cellulose or collagen. Preferably, the support matrix is an extracellular support matrix. As used herein, the phrase "extracellular support matrix" means a solid, such as a gel or sponge, comprising one or more organic molecules or molecular aggregates, which molecules or aggregates are those produced and secreted by cells into the extracellular space and which serve, in vivo, as a support, adhesive and framework for maintaining three-dimensional tissue organization and function. Exemplary of such molecules are high-molecular weight proteins and glycoproteins such as collagen, laminin, fibronectin and the like, complex polysaccharides and the like molecules.

In a preferred embodiment, the extracellular support matrix is a collagen-containing gel. Exemplary collagen-containing gels are gelatinized pork skin such as GELFOAM™ (The Upjohn Company, Kalamazoo, Mich.) and a composition comprising laminin, collagen, proteoglycan and entactin such as MATRIGEL™ (Collaborative Research, Inc., Bedford, Mass.). GELFOAM™ is a patented product described in U.S. Pat. No. 2,465,357, the disclosure of which is incorporated herein by reference.

In another preferred embodiment, the extracellular support matrix is a homopolysaccharide sponge. Leighton, J., *J. Nat'l Cancer Instit.*, 12:545–561 (1951). A preferred homopolysaccharide is cellulose. Homopolysaccharide sponges contemplated by the present invention are not limited as to weave or net size.

In still another preferred embodiment, the extracellular support matrix comprises a combination of a collagen-containing gel and a homopolysaccharide sponge. Preferably, such a combination comprises a top layer of a collagen-containing gel and a bottom layer of a homopolysaccharide sponge. The collagen-containing gel is preferably gelatinized pork skin and the homopolysaccharide is preferably cellulose. In a particularly preferred embodiment, the support matrix comprises a combination of a top layer of GELFOAM™ and a bottom layer of a cellulose sponge, which matrix has been shown to be most effective in maintaining normal hair growth of histocultured skin.

There are no set ratios of skin sample size to size of the extracellular support matrix. The matrix can be anywhere from a diameter which is sufficient to support the skin sample to being greater in size and substantially overlapping the skin sample. Multiple samples can be placed on the same matrix so long as the skin samples are not actually touching. A preferred distance between skin samples is about 1 to 2 mm.

The skin sample is placed on the matrix such that the internal surface of the skin is adjacent to the matrix and the external surface of the skin is facing away from the matrix. In a preferred embodiment, the internal surface of the skin is in contact with the matrix. In this arrangement, the external surface of the skin is available for contacting with toxins or other compositions to assess their effect on the skin according to the present methods.

The matrix with the skin sample thereon is immersed in a volume of a medium sufficient to contact the matrix but not to completely cover the skin; i.e. the external surface of the skin is not submerged but is exposed above the surface of the medium. Preferably, the surface of the medium is within 0.5 to 2 mm of the upper surface of the matrix and provides aqueous contact to the skin sample through a wicking effect. For example, where the skin sample has a thickness of about 1 to 2 mm, the surface of the medium is preferably from about 0.5 to about 2 millimeters below the external surface of the skin.

The extracellular support matrix is typically soft and may indent upon placement of the skin sample thereon such that the edges of the matrix may contact the vertical edges of the skin sample.

The extracellular support matrix is pre-treated to equilibrate the matrix with the medium before the skin sample is placed thereon. Pretreatment of the matrix comprises cutting the matrix to a predetermined size and soaking the cut matrix in the medium in a sterile container for a period of time sufficient to saturate and equilibrate the matrix with the medium. A preferred soaking time is 4 hours at 37° C.

The medium contemplated by the present invention is an aqueous nutrient medium designed to promote and maintain viability of the skin sample. A preferred medium is Eagles Minimum Essential Medium (MEM) supplemented with 10% (v/v) fetal bovine serum (FBS) and an antibiotic. Exemplary antibiotics are gentamicin, streptomycin, penicillin, kanomycin and the like. A preferred antibiotic is gentamicin. The final concentration of antibiotic in the medium depends upon the particular antibiotic used. Where the antibiotic is gentamicin, a preferred concentration is about 0.2 mgs per ml of medium. Other media can also be used, preferably involving the use of fetal bovine serum, or using serum-free defined mediums as is well known in the art.

The matrix with the skin sample thereon may be maintained in the medium for indefinite periods of time. Preferably, the medium is changed every 2 to 3 days.

After a suitable histoculturing period, a quantity of liposomes containing the selected beneficial macromolecular compound is applied to the skin histoculture. A second histocultured skin sample is treated with the compound alone as a control. The skin histocultures are then processed and prepared to asses the viability of the tissues in the skin cell undergoing the treatment, and to determine the specificity of delivery of the beneficial compound in the liposomes.

In one embodiment, viability and/or delivery is assessed by measuring the incorporation into cells of the skin sample of an indicator specific for viable cells. As used herein, the phrase "specific for viable cells" means that the indicator is taken up or incorporated into living, but not dead, cells.

The indicator specific for viable cells may be a metabolic precursor or a non-metabolite that gains access to living cells. Exemplary metabolic precursors are ribo- or deoxyribonucleic acid precursors such as purines, pyrimidines, nucleosides and nucleotides. Preferably, the metabolic precursor is operatively linked to an indicating means to facilitate detection. A preferred indicating means for a metabolic-precursor indicator is a radiolabel such as $^{35}S$, $^{32}P$, $^{125}I$, $^{3}H$ and the like. A particularly preferred radiolabeled metabolic-precursor indicator is $^{3}H$-thymidine.

A preferred non-metabolite indicator specific for viable cells is a dye that is capable of optical detection. Any dye recognized in the art as being specific for viable cells can be used in accordance with the skin toxicity assay of this invention. See, e.g., Handbook of Fluorescent Probes and Research Chemicals, ed. by R. P. Haugland, Molecular Probes, publisher, Eugene, Oreg. (1989–1991 and 1992–1993).

In a preferred embodiment, the dye is a fluorescent dye. Exemplary viable-cell-specific fluorescent dyes are BCECF-AM (B-1150), Calcein-AM (C-1430), CFDA (carboxyfluorescein diacetate; C-195) Acridine orange (A-1301), Calcein blue (H-1426), Fura-2AM (F-1201), Fluorescein diacetate (F-1303) or Carboxy analog (C-1431) and the like. Such dyes are well known in the art and are commercially available (Molecular Probes, Eugene Oreg.). Particularly preferred are the dyes BCECF-AM or Calcein-AM. The numerals in the parenthesis indicates the product number for the listed fluorescent dyes that are available from Molecular Probes.

In one embodiment, the incorporation or uptake of fluorescent dyes specific for viable cells depends upon metabolic activity of the viable cell. In accordance with this embodiment, non-fluorescing dyes are taken up by viable cells and converted to a fluorescing product by an intracellular enzyme such as an esterase. The presence of intracellular fluorescence indicates viability.

In another embodiment, viability is assessed by measuring the uptake or incorporation into cells of the skin sample of an indicator specific for dead cells. As used herein, the phrase "specific for dead cells" means that the indicator is taken up or incorporated only into dead, non-viable cells.

Typically, dyes specific for dead cells are compounds with a high ionic charge and low permeability such that the dyes cannot permeate intact cellular membranes. When cells die, the membrane is structurally or functionally ruptured such that dyes specific for dead cells gain access to the intracellular space where they bind to intracellular components such as nuclear membranes.

A preferred dead-cell-specific indicator is a dye capable of optical detection. A preferred dead-cell-specific dye is a fluorescent dye such as propidium iodide, ethidium bromide, ethidium homodimer [(5,5'-diazadecamethylene) bis (3,8-diamino-6-phenyl-phenanthridium) dichloride, dihydrochloride] and the like. most preferred is propidium iodide. Propidium iodide (PI) and other dyes specific for dead cells are well known in the art and commercially available (Molecular Probes, Eugene, Oreg.).

In still another preferred embodiment, assessing viability is accomplished by simultaneously measuring the uptake or incorporation of both an indicator specific for viable cells and an indicator specific for dead cells. Viability is assessed as the ratio of viable to dead cells. Where both the indicator specific for viable cells and the indicator specific for dead cells are fluorescent dyes, such dyes should have different emission spectra so as to facilitate discrimination between viable and dead cells. Compositions and methods for determining cell viability by the differential uptake of indicators specific for viable and dead cells and tissue culture samples are well known in the art. Haugland, Supra.

Means for detecting the uptake or incorporation of indicators specific for viable cells are dependent upon the particular indicator used and are well known to those of skill in the art. A preferred means for detecting radiolabeled metabolic-precursors is autoradiography of histological sections of the skin samples that have taken up the precursor.

A preferred means for detecting dyes is microscopic examination. Microscopic examination can involve the use of any microscope that allows one to selectively and reproducible evaluate indicator incorporation into specific cells of the skin sample at varying locations within the three-dimensional, native-state skin histoculture.

Typically, the microscopic examination requires the capability of optical sectioning. Optical sectioning is the ability to view preselected depths within the three-dimensional structure of the skin in the absence of optical interference provided by the presence in the skin of microsomes, air bubbles, fat globules and other tissue components, which provide reflection of light and optical interference.

In addition, optical sectioning allows for viewing a variety of planes within the three-dimensional skin histoculture. By sequentially sectioning serial layers of the skin, one can produce a total picture of the skin and hair follicle or, alternatively, a picture of a region of the skin and the follicles where a particular cell type of interest is located. Thus, comparative studies of a plurality of depths or regions of the skin can be made. In this way, viability can be assessed in surface cells, at cells underneath the dermal layer, cells inside the epidermal layer, or in other specific cell types such as nerve cells, oil secreting cells, hair follicle cells.

The optical section thickness can be varied to accommodate the cell size or tissue to be observed and can range from about 0.1 to 1000 microns. Preferred sections are in the range of 0.5 to 10 microns, preferably about 2 to 6 microns.

A preferred microscope that is capable of performing optical sectioning is a confocal scanning laser microscope such as the MRC-600 CONFOCAL IMAGING SYSTEM (Bio-Rad, Richmond, Calif.), mounted on a Nikon Optiphot using a 10× PlanApo plan objective. Such a confocal scanning microscope has been successfully used to asses delivery (see the Examples). Other available methods for optically scanning or sectioning planes of the tissue sample are also contemplated by the present invention.

Viability is assessed at any particular location within the skin as a ratio of viable or dead cells to total cells or as a ratio of live to dead cells on the basis of the uptake of indicators specific for viable and dead cells respectively. When viability is assessed both before and after contact with a putative beneficial compound, comparing the ratio of live to dead cells as assessed before and after contact with the putative beneficial agent provides an indication of the toxicity or benefit provided by the administered compound.

The procedure for applying indicators to the skin culture varies with the particular indicator used. Typically, indicators are added to the medium about 6 hours and, preferably about 24 hours after placing the skin sample in the medium. Following addition of the indicator to the medium, the culture is maintained under culturing conditions for a period time sufficient to allow the indicator to enter and label the cells of the skin sample. Preferably, the culture is maintained in the presence of the indicator for about 5 minutes to about 2 hours and, more preferably for about 10 to 20 minutes.

The concentration of indicator added to the medium varies with the particular indicator used. Where the fluorescent dyes PI and BCECF-AM are used, the dye concentration is from about 1 to about 100 micromolar, preferably from about 2 to about 50 micromolar, and more preferably about 5 micromolar each.

Exemplary in vitro skin histoculture methods are described in the Examples.

Results of studies herein on liposome-mediated delivery show that the beneficial macromolecular compound is concentrated at the hair follicles and has been transported across the cell membrane and through the cytoplasm to the nucleus. The liposome-incorporated material (beneficial compound) is preferentially delivered to the hair follicle, because the levels of the beneficial compound in the adjacent skin tissue is substantially lower than in the hair follicles. Due to the unusual selectivity of delivery to the hair follicle when using the disclosed liposome formulations, and based on the degree of selectivity based on the compound to be delivered and the liposome formulation utilized, this selectivity is referred herein to as "directed delivery", "preferential delivery", "selective delivery" and in some cases as "exclusive delivery", depending upon the relative amount of material delivered to the hair follicle tissue as compared to the adjacent skin tissue. In addition, the selectivity can be expressed in terms of the selectivity of pharmaceutical effect upon the hair follicle tissue as compared to the adjacent skin tissue.

With the tissue sample treated with the macromolecular compound where the compound had not been incorporated in liposomes, very little reaches the follicle cell or follicle cell nuclei. Thus, the liposome-based system specifically, selectively, and efficiently targets the hair follicles with compounds that otherwise do not concentrate at the hair follicles.

The in vitro histoculture assay can be utilized in a variety of ways. The assay can be utilized to evaluate and optimize liposome formulations for enhanced efficacy of delivery of the beneficial compound, or to study other aspects of the liposomes usefulness in the targeting formulation. Furthermore, the assay can be used as a screening system to identify additional beneficial compounds for treating conditions afflicting hair follicles as described further herein.

2. Preparation of Liposomes Encapsulating Beneficial Compounds

A beneficial liposome composition of the invention is typically provided in one or more of a variety of compositional forms suitable for the contemplated use. Although proteins, nucleic acids or other compounds for use in a liposome generally retain biological activity in a variety of buffers and solutions, it is preferred to be formulated in a phospholipid composition. Particularly preferred are phospholipid compositions which afford maximum stability and biological activity of the beneficial compound in the composition. Such phospholipid compositions are preferably formulated to form liposome compositions, as are generally well known in the art. Typically, the composition contains an amount of biologically active beneficial compound suitable for its contemplated use.

The preparation of liposomes, and their use in drug therapy has been previously described. See, for example, U.S. Pat. Nos. 4,241,046, 4,394,448, 4,529,561, 4,755,388, 4,828,837, 4,925,661, 4,954,345, 4,957,735, 5,043,164, 5,064,655, 5,077,211 and 5,264,618, the disclosures of which are hereby incorporated by reference. Exemplary methods for the entrapment of nucleic acids into liposomes is described in U.S. Pat. No. 5,223,263.

Preferred and exemplary methods for preparing beneficial compound-encapsulated liposomes for use in the present methods are described in the Examples. In particular, the encapsulation of protein, and the encapsulation of nucleic acid, each for delivery to hair follicles as a beneficial compound are described herein.

The liposome compositions of the present invention typically comprise about 0.1 mg to about 3 mg of protein, or about 0.1 ug to about 0.5 mg nucleic acid, per mg of phospholipid mixture.

The ratio of active compound to phospholipid mixture may determine the sensitivity of the resulting reagent. Thus, use of a ratio of about 1 to 2 mg protein per mg phospholipid mixture may be suitable for a protein reagent having a International Sensitivity Index ("ISI") of about 1.0. Use of a ratio of about 0.25 to about 0.5 mg protein per mg phospholipid mixture may be suitable to prepare a composition having an ISI of about 1.6 to about 2.0.

Preferred are compositions that additionally comprise from about 0.5 to about 1.5% (w/v) glycine. Where it is desired to be able to lyophilize the liposome composition to allow storage and later reconstitution, the reagent preferably includes a cryopreservative, preferably a carbohydrate preservative, most preferably trehalose.

The lipid bilayer of the liposomes comprises phospholipids, preferably, phosphoglycerides. Exemplary liposome compositions include phosphatidylcholine (PC) liposomes, particularly egg PC (EPC) and dipalmitoyl PC (DPPC). Additional candidate liposome compositions are prepared according to the teachings of U.S. Pat. No. 4,394,488, the teachings of which are incorporated by reference, particularly the descriptions of liposomes comprising phosphotidylethanolamine (PE), phosphotidylserine (PS), sphingolipids, phosphotidylglycerol (PG), phosphatidic acid (PA), cholesterol, spingomyelin cardiolipin, various cationicphospholipids glycolipids, gangliosides, cerebrosides and the like, used either singularly or in combination.

"Phospholipid" refers to an organic molecule derived from either glycerol (most commonly) or sphingosine. Phospholipids derived from glycerol (or phosphoglycerides) comprise a glycerol backbone, two fatty acid chains esterified to the first and second carbons of the glycerol and phosphoric acid esterified to the third carbon. Optionally, an alcohol moiety is esterified to the phosphoric acid.

Suitable phospholipids for use in the liposome compositions of the present invention include those which contain fatty acids having twelve to twenty carbon atoms; said fatty acids may be either saturated or unsaturated. The phospholipids may come from any natural source and the phospholipids, as such, may be comprised of molecules with differing fatty acids. Phospholipid mixtures comprising phospholipids from different sources may be used. For example, PC, PG and PE may be obtained from egg yolk; PS may be obtained from animal brain or spinal chord. These phospholipids may come from synthetic sources as well.

Phospholipid (PL) mixtures having a varied ratio of individual PLs may be used. However, although the phospholipids may be used in varied ratios, mixtures of phospholipids having preselected amounts of individual phospholipids result in liposome compositions having advantageous activity and stability of activity. Thus although a wide range of ratios of individual phospholipids may be used, for advantageous activity and stability of the resulting liposome composition, certain phospholipid compositions are preferred.

The phospholipids are conveniently combined in the appropriate ratios to provide the PL mixture for use in preparing the liposome composition of the present invention.

Liposomes are preferably prepared using one or more phospolipids including (N-(1-(2,3-dioleolyoxy)propyl)-N,N,N-trimehtyl ammonium chloride) (DOTMA), dioleoylphosphatidylethanolamine (DOPE), dioleoylphosphatidylcholine (DOPC), phosphatidylethanolamine (PE), egg PC (EPC), phosphatidylcholine (PC), dipalmitoyl PC (DPPC), cholesterol and the like phospholipids. Phospholipids can be obtained from a variety of sources, including Avanti (Birmingham, Ala.), GIBCO BRL (Gaithersburg, Md.) and Aldrich (Milwaulkee, Wis.), or can be prepared from available materials, as is well known.

Preferred liposomes comprise PC, EPC, or DPPC homogeneously. Further preferred liposome compositions comprise a combination of a PC-type phospholipid (such as PC, EPC, DOPC, DPPC and the like) combined with a PE-type phospholipid (PE, DOPE and the like) in a molar ratio of from about 2:5 to about 5:2, more preferably about 5:2 PC:PE. A preferred liposome composition comprises PC:PE:Chol in a molar ratio of 5:2:3.

A preferred liposome for use in the present invention additionally includes cationic phospholipids. One preferred cationic phospholipid is a monocationic phospholipid having two identical alkyl side chains.

Preferred cationic phospholipids are also generally available from a variety of sources, including the above recited sources. Particularly preferred cationic phospholipids include cationic phospholipids such as D282, D378, D383, D3886, D3897 and D3899, obtainable from Molecular Probes (Eugene, Oreg.), the structure and synthesis of which is well known and described in Handbook of Fluorescent Probes and Research Chemicals, ed. by R. P. Haugland, Molecular Probes, publisher, Eugene, Oreg. (1989–1991, and 1992–1993). The structures of cationic phospholipids D282, D378, D383, D3886, D3897 and D3899 are shown in FIG. 8.

D282 is also known as 1,1'-dioctadecyl-3,3,3',3'-tetramethylindocarbocyanine perchlorate; D378 is also known as 3,3'-diheptyloxacarbocyanine iodide; D383 is also known as 1,1'-didodecyl-3,3,3',3'-tetramethylindocarbocyanine perchlorate; D3886 is also known as 1,1'-dioleyl-3,3,3',3'-tetramethylindocarbocyanine methanesulfonate; D3897 is also known as N-4-(4-dilinoleylaminostyryl)-N-methylpyridinium iodide; and D3899 is also known as 1,1-dilinoleyl-3,3,3',3'-tetramethylindocarbocyanine perchlorate.

In one embodiment, the liposome composition of this invention contains one or more of the above cationic phospholipids. Preferably, a liposome composition of this invention comprises a formulation of phospholipids comprising a mixture of (a) one or more of the phospholipids PC, EPC, DOPC, DPPC, PE, DOPE, cholesterol and the like phospholipids, and (b) one or more of the cationic phospholipids D282, D378, D383, D3886, D3897, D3899 and the like. A particularly preferred liposome composition comprises a mixture of phospholipid (a) and cationic phospholipid (b) in a ratio of about 0.5 to 2.0 moles of phospholipid (a) to about 0.5 to 1.5 moles of phospholipid (b), and more preferably about 1.0–1.2 moles of phospholipid (a) to 0.8 moles of cationic phospholipid (b). A preferred phospholipid composition in this embodiment comprises a mixture of DOPC or DOPE with one or more of the above cationic phospholipids in a ratio of about 0.8 moles to about 1.0–1.2 moles.

In another embodiment, the invention comprises a liposome composition comprising one or more phospholipids selected from the group consisting of PC, EPC, DOPC, DPPC, PE, DOPE and cholesterol, combined with one or more phospholipids to form pH-sensitive liposomes. pH-sensitive liposomes are generally well known and their preparation has been described by Straubinger et al., *FEBS Letts.*, 179:148–154 (1985). A preferred pH sensitive liposome comprises oleic acid (OA) and PE at a mole ratio of 3:7. OA is available from a variety of commercial sources, including Sigma (St. Louis, Mo.).

Where the liposome composition will be lyophilized prior to storage for later use, it is preferred to include a carbohydrate or carbohydrates as cryopreservative(s) to protect the integrity of liposomes in the resulting liposome composition during lyophilization and subsequent rehydration.

Cryopreservation relates to preserving the integrity of delicate substances when liquids containing them are frozen and dehydrated. The use of a carbohydrate as a cryopreservative of liposome integrity upon freezing and subsequent lyophilization has been reported. Racker, E., Membrane Biol., 10:221–235 (1972); Sreter, F. et al., Biochim. Biophys. Acta., 203:254–257 (1970); Crowe et al., Biochem. J., 242:1–10 (1987); Crowe et al., Biochim. Biophys. Acta., 987:367–384 (1988).

Suitable carbohydrate cryopreservatives include trehalose, maltose, lactose, glucose and mannitol. According to a preferred aspect of the present invention, trehalose is included in aqueous buffer solution used in the preparation of a liposome composition of the present invention (prior to lyophilization), preferably at a concentration in the range of about 50 mM to about 250 mM.

The phospholipids, which may be obtained from the manufacturer in an organic solvent, are mixed together in the appropriate ratios to yield the specified composition. An antioxidant can also be added to reduce alkyl chain peroxidation of the fatty acid portions of the phospholipids, and the organic solvent, if present, is removed by evaporation. One suitable antioxidant is butyrated hydroxy toluene. Preferably about 0.1% (by weight) of antioxidant is used.

The dried (evaporated) phospholipid mixture is then redissolved with an aqueous detergent solution. Suitable detergents include those which have a relatively high critical micelle concentration (CMC). Womack et al., Biochim. Biophys. Acta, 733:210 (1983). Such detergents include detergents having a CMC of greater than approximately 2 mM. Preferred are those detergents having a CMC of between approximately 2 to 25 mM. Such preferred detergents include 3-[(3-cholamidopropyl)-dimethylammonio]-1-propanesulfonate (CHAPS) and alkylglucopyranosides such as octyl beta-D-glucopyranoside, octyl beta-D-thioglucopyranoside and the like. Optionally, the detergent solution may include other components. These components may include buffer salts such as HEPES, Tris, phosphate, and the like; various other salts such as NaCl, KCl, and the like; a carbohydrate cryopreservative such as trehalose, maltose, glucose, and the like; and glycine.

According to a preferred embodiment of the present invention, the detergent solution comprises 20 mM Tris, pH 7.5, 150 mM NaCl, (TBS) containing 100 mM CHAPS, 150 mM trehalose and 0.8% glycine. According to this preferred embodiment, the phospholipids are redissolved in this solution to give a final concentration of about 20 mg/ml.

Purified proteins for use in a liposome, together with carrier protein, are combined with the redissolved phospholipids and the volume of the resulting mixture is adjusted with a buffer as described above, preferably containing cryopreservative (most preferably trehalose) and glycine but no detergent. Protein is admixed with carrier protein, such as bovine gamma globulin, and sufficient buffer is added to adjust the final concentrations of active protein to 10 mg/ml, bovine gamma globulin to 1 mg/ml, phospholipid to 4 mg/ml and detergent to 20 mM. Suitable buffers include TBS containing 150 mM trehalose and 0.8% glycine.

The resulting clear, colorless solution requires no vortexing or sonicating to ensure co-solubilization.

The detergent in the phospholipid admixture can be removed by a number of methods resulting in a stable liposome composition having a protein or nucleic acid associated with and inserted through the lipid bilayer. Suitable methods of removal of detergent include dialysis, tangential flow diafiltration, cross flow hollow fiber filtration, treatment with hydrophobic chromatography resin, and simple dilution.

One preferred method of detergent removal from the phospholipid admixture utilizes dialysis for at least 30 hours at room temperature in dialysis membrane tubing against a buffer such as TBS containing 150 mM trehalose, 0.8% glycine and 0.05% NaN$_3$ to remove the detergent. Another preferred method of detergent removal utilizes resin treatment. Suitable resins include hydrophobic chromatographic resins such as Amberlite XAD-2 (Rohm and Haas Co. in Philadelphia, Pa.) or Bio-Beads SM-2 (BioRad in Richmond, Calif.). The resins may be used to remove the detergent, either by direct contact with the phospholipid solution admixture or separated from it by a dialysis membrane. The rate of removal of detergent from the phospholipid admixture is proportional to the weight ratio of the detergent in solution and the chromatographic resin beads.

The liposome solution resulting from the detergent removal step is then made to 5 mM CaCl$_2$. According to one preferred aspect, the liposome composition which contains the fully active compound is diluted to a concentration of 50 mM Tris, pH 7.5, 75 mM trehalose, 0.8% glycine and 10 to 15 mM CaCl$_2$ before use. Alternatively, the diluted reagent may be lyophilized for long term preservation of its biological performance characteristics and then later reconstituted by suspension in water before use.

Another preferred method of detergent removal avoids the use of either dialysis or resin treatment and yet provides for preparation of active reagent. According to this method, detergent solubilized phospholipid compositions containing protein or nucleic acids are diluted into a buffer without detergent to produce mixed micelles containing the beneficial compound which remain capable of being fully activated by CaCl$_2$. According to this aspect of the invention, phospholipids are dissolved to 20 mg/ml in a buffer containing detergent, preferably an alkyl glucopyranoside. A suitable buffer-detergent solution comprises 20 mM HEPES (pH 6) containing 50 mM octyl beta-D-thioglucopyranoside (OTG) and 150 mM NaCl. Carrier protein, active protein or nucleic acid, and CaCl$_2$ are then added and the mixture diluted further with buffer without detergent, such as 20 mM HEPES (pH 6) containing 150 mM NaCl, to yield final concentrations of active protein or nucleic acid at about 10 mg/ml, carrier protein (bovine gamma globulin) at 1 mg/ml, CaCl$_2$ at 5 mM, phospholipids at 4 mg/ml, and OTG at 10 mM. The reagent may be lyophilized for storage as described above, or diluted as described above before use.

According to another aspect of the present invention, this reagent may be prepared by following methods for the preparation of vesicles and detergent-phospholipid mixed micelles from phospholipids by methods based on mechanical means, by removal of organic solvents, by detergent removal, and by size transformation as has been described by Lichtenberg, D. and Barenholz, Y., Methods of Biochemical Analysis, 33:337–462 (1988), and the disclosures of which are incorporated herein by reference.

Incorporation of a beneficial compound is conducted by incorporation of the compound in the liposome either during liposome formation, or after formation by combining the liposome with the compound. Methods of introducing the compound into the liposome can vary, and are not intended to be limiting. Preferred methods are described in the Examples.

Where nucleic acid is entrapped into a phospholipid composition, a wide variety of ratios of nucleic acid to phospholipid may be utilized as discussed earlier. However, it is preferred to use about 100 micrograms (ug) of nucleic acid (in the form of double-stranded DNA such as plasmid DNA) with about 0.1 to 10.0 milligram (mg) phospholipid. Where cationic phospholipids are to be utilized in a phospholipid composition, it is particularly preferred to use about 100 ug nucleic acid to from 0.2 to 1.2 micromoles (umole) of phospholipid, particularly 100 ug nucleic acid to 0.8 umole.

3. Hair Follicle-Targeted Drug Therapy

In one embodiment, the invention describes methods for selective and beneficial targeting of therapeutic compounds and compositions to the hair follicle of a mammal.

Based on the present disclosure, it is determined that compounds and compositions, particularly proteins, nucleic acids and other large macromolecules, are specifically delivered to hair follicle tissue, so long as the compounds or compositions are encapsulated in liposomes.

The invention contemplates the delivery of a wide variety of beneficial or otherwise therapeutic compounds to the hair follicle, with the selectivity of delivery to the hair follicle over adjacent skin tissue cells being of particular importance, and the primary result according to the present methods. Thus, the therapeutic compounds can be nucleic acids, hormones, proteins, enzymes, vitamins and other biochemical co-factors deemed to provide a therapeutic effect upon the hair follicle cell's growth, condition, color and the like.

Particularly preferred are agents which improve the growth of the hair shaft, agents which stimulate the production of hair coloring pigments in the hair follicle, agents which replace pigment in the follicle cell or hair shaft (i.e., restore hair color), agents which stimulate hair growth, and agents which prevent hair loss.

Agents useful for pigmenting hair color include the protein melanin, which directly colors hair as a pigment, and the protein tyrosinase, which is an enzyme which catalyzes the production of melanin pigment precursors and thereby increases pigment production in hair follicle cells, and nucleic acids which encode and express tyrosinase and other proteins which stimulate hair growth or prevent hair loss.

Agents useful in conditions of hair loss (alopecia) are those which stimulate hair growth, or those which inhibit the hair loss. Hair growth stimulators are generally well known, and include minoxidil, substance-P, cyclosporin and the like known hair growth stimulators.

A preferred embodiment involves the prevention of hair loss (alopecia) during chemotherapy where a patient experiences chemotherapy-induced hair loss due to the effect of the chemotherapeutic agent on the hair follicle and surrounding tissue. Thus the invention contemplates the use of inhibitors of the deleterious effects of a chemotherapeutic agent. By virtue of the selective application of the inhibitor to the hair follicle by the liposome-mediated delivery methods of the present invention, inhibition of a chemotherapeutic agent is localized to the hair follicle and therefore does not interfere with the intended systemic activity of the administered chemotherapeutic agent. In this embodiment, a preferred inhibitor of chemotherapy-induced alopecia is a gene product of the multiple drug resistance (MDR) gene, preferably the p-glycoprotein expressed by the human MDR-1 gene. Administration of a nucleic acid comprising an expression vector capable of expressing human p-glycoprotein via liposomes to the hair follicle provides intracellular human p-glycoprotein, and reduces the toxic effects of the chemotherapy upon the hair follicle, thereby reducing alopecia induced by the chemotherapy.

Another embodiment contemplates the use of the human transformation growth factor-alpha (TGF-$\alpha$) gene to reverse the "wavy" hair phenotype. See for example, Mann et al., Cell, 73:249–261 (1993), and Luetteke et al., Cell, 73:263–278 (1993). Therefore the invention contemplates the use of a cDNA expression vector that expresses the TGF-$\alpha$ gene as a beneficial compound to reduce the incidence of wavy hair where the deficiency of TGF-$\alpha$ gene is the cause of the wavy hair phenotype.

The invention additionally contemplates the administration of any gene beneficial to hair follicles. A gene is beneficial to hair follicles where it confers, upon selective delivery to the hair follicles by the present methods, a beneficial effect upon the hair follicle. Exemplary beneficial genes include genes normally and preferentially expressed in hair follicle, and therefore important for normal gene function. Beneficial genes can be identified by any of a variety of molecular biological methods. For example, a cDNA library of expressed genes can be prepared from hair follicle tissue supporting healthy hair, and can be enriched by subtractive hybridization against a cDNA library derived from a non-hair-producing or vellus-hair-producing follicle tissue, thereby producing a library of cDNA molecules whose expression is specific to hair follicles. Individual cDNA molecules from the hair specific cDNA library can be further screened for therapeutic effectiveness using the skin histoculture assay described herein.

Particularly preferred is a gene capable of stimulating hair growth, referred to as a hair growth stimulating gene. A hair growth stimulating gene is any nucleic acid which stimulates hair growth upon administration of the gene to hair follicles of skin according to the present liposome-mediated delivery methods. A hair growth stimulating gene can be prepared from the hair specific cDNA library described above. The hair growth stimulating gene can be selected from the hair specific cDNA library by a variety of methods. The gene can be identified by subtractive hybridization using a cDNA library prepared from skin tissue which has vigorous hair shaft production against a cDNA library prepared from skin tissue which is deficient in vigorous hair shaft production, such as patches of skin where hair is absent or thinning. Such areas of skin have hair follicles but the follicle cells are experiencing changes in gene expression which effect the condition of the hair, particularly the rate of hair shaft growth. The resulting cDNA library following subtractive hybridization against the hair growth deficient cDNA library is further screened in the in vitro skin histoculture assay for cDNA molecules capable of stimulating hair growth to identify hair growth stimulating genes. Methods for isolating cDNA libraries and for conducting subtractive hybridization a well known in the art, and are not to be considered as limiting to the present invention.

The therapeutic agent can be delivered to the hair follicle in the form of an active formulation, such as the pigmentation protein or enzyme itself, or can be provided through gene replacement therapy, where a nucleic acid is introduced that expresses the protein to be delivered. In this mode, also referred to as gene therapy, a replacement therapy protein is provided which exerts a beneficial effect. The protein is referred to as a "replacement therapy" protein to connote that the therapy administered is to reconstitute (replace) into the tissue a protein-based function not previously present. It does not mean that a gene or protein was first deliberately removed, and then replaced.

A therapeutic amount of a therapeutic protein in a liposome composition of this invention is an amount sufficient to produce the desired result, and can vary widely depending upon the disease condition and the potency of the therapeutic compound.

Thus, in one embodiment, the invention contemplates a method for directly and selectively delivering a beneficial compound to the hair follicles of a mammal comprising the steps of:

a) incorporating an effective amount of at least one selected beneficial compound into a liposome; and b) applying said liposomes to skin areas of the mammal having a plurality of hair follicles;

whereby said beneficial compound is preferentially transmitted to said hair follicles and enters into said hair follicles.

As described, the beneficial compound can be a protein, a nucleic acid or other molecule having desirable properties upon delivery to the hair follicle cell. Where the compound is a protein, such as tyrosinase or aromitase, the objective is to color hair, or to stimulate hair growth. Alternatively, the compound can be the pigment melanin where the objective is to restore hair color as demonstrated herein. Alternatively, the compound can be a nucleic acid encoding tyrosinase, aromitase, p-glycoprotein, TGF-$\alpha$, a hair growth stimulating gene or other beneficial proteins, or can encode and express an antisense or ribozyme nucleic acid as discussed herein.

Thus, in a related embodiment, the invention contemplates a method for restoring hair color to the hair of a mammal comprising applying a therapeutically effective amount of a liposome composition to a skin area on the mammal populated with hair follicles. The liposome composition contains an effective amount of a beneficial compound capable of restoring hair color. The compound can be the pigment melanin, can be the protein tyrosinase, or can be a nucleic acid capable of expressing a tyrosinase cDNA as described herein.

In a related embodiment, the invention contemplates a method for inhibiting chemotherapy-induced alopecia in a mammal undergoing chemotherapy comprising applying a therapeutically effective amount of a liposome composition to a skin area on the mammal populated with hair follicles. The liposome composition contains an effective amount of a beneficial compound capable of inhibiting within the follicle cell environment the toxic effects of the chemotherapy. Any compound that inhibits chemotherapy toxicity is contemplated, although the MDR-1 gene product (p-glycoprotein) is particularly preferred.

The method can be practiced on a variety of mammals, including agricultural stock such as cow, sheep, horse, goat, pig, and the like, pets such as cats, dogs or other domesticated mammals, and humans. Typically, the hair follicle is present in the skin of a mammal, and the method is practiced in vivo on a living mammal for the purpose of benefitting the condition of the hair follicle or hair shaft of the mammal.

In one embodiment, the selected beneficial compound is a protein which affects hair growth, alopecia, hair color or hair condition. Preferred are the proteins tyrosinase or aromitase, as well as nucleic acids coding for hair modifying proteins. In a related embodiment, the selected beneficial compound is a pigment, such a melanin.

Melanin and tyrosinase are preferred for their role in coloring hair. Aromitase is preferred for its role in stimulating hair growth. Other therapeutic compounds suitable for use in stimulating hair growth in conditions of alopecia include cyclosporin analogs, substance P, estrogen analogs and anti-androgens. Therapeutic compounds suitable for use in preventing hair growth, such as facial or pubic hair, include alopecia inducers, catagen blockers, epidermal growth factor, and the like inhibitors of hair growth.

In another embodiment, the selected beneficial compound is a nucleic acid capable of expressing a beneficial protein which affects hair growth, alopecia, hair color or hair condition as described earlier. Preferred are the nucleic acids that express the proteins tyrosinase, aromitase, or other hair-growth stimulators, the protein products of the MDR-1 gene (i.e., p-glycoprotein) to prevent chemotherapy-induced alopecia, or enzymes which synthesize those proteins.

In one preferred embodiment, the invention contemplates a method for restoring hair color in mammals, particularly man, in which the hair color is greying for any of a variety of reasons, including age. The method comprises applying a therapeutically effective amount of a liposome composition of this invention to a skin area on the mammal having a plurality of hair follicles which exhibit fading or greying hair color. The liposome composition preferably contains an amount of a nucleic acid capable of expressing human tyrosinase in the cells of the hair follicles. Preferably, the nucleic acid encodes a human tyrosinase gene including the nucleotide sequence characteristics of the tyrosinase gene sequence shown in SEQ ID NO 1.

In one embodiment, the application of the tyrosinase-gene containing liposome composition can be repeated at defined intervals to provide prolonged effectiveness, as needed.

Insofar as a liposome composition of this invention is used therapeutically, the liposome composition is itself a therapeutic composition, and as such may also contain additional components.

Therapeutic compositions of the present invention contain a physiologically tolerable carrier together with at least one species of liposome composition of this invention as described herein, dispersed therein as an active ingredient. In a preferred embodiment, the therapeutic composition is not immunogenic when administered to a human patient for therapeutic purposes.

As used herein, the terms "pharmaceutically acceptable", "physiologically tolerable" and grammatical variations thereof, as they refer to compositions, carriers, diluents and reagents, are used interchangeably and represent that the materials are capable of administration upon a mammal or human without the production of undesirable physiological effects such as nausea, dizziness, gastric upset and the like.

The preparation of a pharmacological composition that contains active ingredients dispersed therein is well understood in the art. Typically such compositions are prepared as sterile compositions either as liquid solutions or suspensions, aqueous or non-aqueous, however, suspensions in liquid prior to use can also be prepared.

The active ingredient can be mixed with excipients which are pharmaceutically acceptable and compatible with the active ingredient and in amounts suitable for use in the therapeutic methods described herein. Suitable excipients are, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient.

The therapeutic composition of the present invention can include pharmaceutically acceptable salts of the components therein (e.g., protein, nucleic acid or other compounds). Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like.

Physiologically tolerable carriers are well known in the art. Exemplary of liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, propylene glycol, polyethylene glycol and other solutes.

Liquid compositions can also contain liquid phases in addition to and to the exclusion of water. Exemplary of such additional liquid phases are glycerin, vegetable oils such as cottonseed oil, organic esters such as ethyl oleate, and water-oil emulsions.

A therapeutic composition contains a liposome composition of the present invention, typically an amount of at least 0.1 weight percent of liposome composition per weight of total therapeutic composition. A weight percent is a ratio by weight of liposome composition to total composition. Thus, for example, 0.1 weight percent is 0.1 grams of liposome composition per 100 grams of total composition.

A therapeutically effective amount of a liposome composition, or beneficial compound therein, is a predetermined amount calculated to achieve the desired effect, i.e., to effectively benefit the targeted hair follicle, depending upon the benefit to be conferred. Thus, an effective amount can be measured by improvements in one or more symptoms associated with the condition of the hair follicle or hair follicle shaft occurring in the patient.

Thus, the dosage ranges for the administration of the liposome composition of the invention are those large enough to produce the desired effect in which the condition in the hair follicle to be treated is ameliorated. The dosage should not be so large as to cause adverse side effects. Generally, the dosage will vary with the age, condition, sex and extent of the disease in the patient and can be determined by one of skill in the art.

The dosage can be adjusted by the individual physician in the event of any complication.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the conditions of administration. Suitable regimes for administration are also variable, but are typified by an initial administration followed by repeated doses at one or more hour intervals by a subsequent administration.

4. Nucleic Acid Expression Vectors for Gene Therapy

In a particularly preferred embodiment, the invention contemplates the use of recombinant DNA molecules that can function as expression vectors for expressing a beneficial protein via a liposome-mediated targeting method of this invention.

"Recombinant DNA (rDNA) molecule" refers to a DNA molecule produced by operatively linking two DNA segments. Thus, a recombinant DNA molecule is a hybrid DNA molecule comprising at least two nucleotide sequences not normally found together in nature. rDNA's not having a common biological origin, i.e., evolutionarily different, are said to be "heterologous".

In living organisms, the amino acid residue sequence of a protein or polypeptide is directly related via the genetic code to the deoxyribonucleic acid (DNA) sequence of the structural gene that codes for the protein. Thus, a structural gene or DNA segment can be defined in terms of the amino acid residue sequence, i.e., protein or polypeptide, for which it codes.

An important and well known feature of the genetic code is its redundancy. That is, for most of the amino acids used to make proteins, more than one coding nucleotide triplet (codon) can code for or designate a particular amino acid residue. Therefore, a number of different nucleotide sequences may code for a particular amino acid residue sequence. Such nucleotide sequences are considered functionally equivalent since they can result in the production of the same amino acid residue sequence in all organisms. Occasionally, a methylated variant of a purine or pyrimidine may be incorporated into a given nucleotide sequence. However, such methylations do not affect the coding relationship in any way.

The DNA segments for use in the present invention are characterized as including a DNA sequence that encodes a beneficial protein as described herein. Particularly preferred segments encode tyrosinase, aromitase, other hair-growth stimulating proteins, melanin, p-glycoprotein, TGF-α, or enzymes that synthesize those proteins. That is, the DNA segments of the present invention are characterized by the presence of a structural gene encoding one or more of the recited beneficial proteins. Preferably the gene is present as an uninterrupted linear series of codons where each codon codes for an amino acid residue found in the beneficial protein, i.e., a gene free of introns.

One preferred embodiment is a DNA segment that codes an amino acid residue sequence that defines a tyrosinase protein corresponding in sequence to a wild type tyrosinase protein and the DNA segment is capable of expressing tyrosinase. A preferred DNA segment codes for an amino acid residue sequence consisting essentially of the tyrosinase encoding nucleic acid sequence. Human tyrosinase gene and its nucleotide sequence is well known including the cDNA sequence for expressing human tyrosinase, and has been described by Tamate et al., *J. Exp. Zool.*, 250:304–311, (1980); Shibahara et al., *J. Exp. Med.*, 156:403–414 (1989); Takeda et al., *Biochem. Biophys. Res. Comm.*, 162:984–990 (1989); Bouchard et al., *J. Exp. Med.*, 169:2029–2042 (1989); and Brichard, *J. Exp. Med.*, 178:489–495 (1993).

Insofar as there is redundancy in the genetic code, it is understood that a variety of nucleotide sequences may be utilized to express a particular amino acid residue sequence. Therefore, in one embodiment, the invention contemplates the use of a nucleotide sequence that encodes a human tyrosinase protein, preferably having the amino acid residue sequence characteristics of the amino acid residue sequence shown in SEQ ID NO 1. A particularly preferred nucleotide sequence for expressing human tyrosinase according to the present invention has the nucleotide sequence characteristics of the nucleotide sequence shown in SEQ ID NO 1.

For expression of the human tyrosinase gene, any of a variety of expression vectors may be utilized so long as the vector is compatible with expression in mammalian cells, particularly human cells. Suitable vectors are well known. A preferred vector is the pRHOHT2 vector described in the Examples, although other mammalian expression vectors are suitable.

Another preferred embodiment is a DNA segment that codes an amino acid residue sequence that defines a multiple drug resistance (MDR) gene product, preferably the MDR-1 gene product designated p-glycoprotein, corresponding in sequence to a wild type p-glycoprotein and the DNA segment is capable of expressing p-glycoprotein. A preferred DNA segment codes for an amino acid residue sequence consisting essentially of the p-glycoprotein encoding nucleic acid sequence. Human p-glycoprotein, the MDR-1 gene and the MDR-1 nucleotide sequence are well known including the cDNA sequence for expressing human p-glycoprotein, and has been described by Chen et a., *Cell*, 47:381–389 (1986); Ueda et al., *J. Biol. Chem.*, 262:505–508 (1987); and Kioka et al., *Biochem. Biophys. Res. Comm.*, 162:224–231 (1989).

Insofar as there is redundancy in the genetic code, it is understood that the invention contemplates the use of a nucleotide sequence that encodes a human p-glycoprotein, preferably having the amino acid residue sequence characteristics of the amino acid residue sequence shown in SEQ ID NO 2. A particularly preferred nucleotide sequence for expressing human p-glycoprotein according to the present invention has the nucleotide sequence characteristics of the nucleotide sequence shown in SEQ ID NO 2.

Another preferred embodiment is a DNA segment that codes an amino acid residue sequence that defines a transforming growth factor-alpha (TGF-α) protein corresponding in sequence to a wild type TGF-α protein and the DNA segment is capable of expressing tyrosinase. A preferred DNA segment codes for an amino acid residue sequence consisting essentially of the TGF-α encoding nucleic acid sequence. Human TGF-α gene and its nucleotide sequence is well known including the cDNA sequence for expressing human TGF-α, and has been described by Jakowlew et al, *Mol. Endocrinol.*, 2:1056–1063 (1988).

Insofar as there is redundancy in the genetic code, it is understood that the invention contemplates the use of a nucleotide sequence that encodes a human TGF-α protein, preferably having the amino acid residue sequence characteristics of the amino acid residue sequence shown in SEQ ID NO 3. A particularly preferred nucleotide sequence for expressing human TGF-α according to the present invention has the nucleotide sequence characteristics of the nucleotide sequence shown in SEQ ID NO 3.

Homologous DNA and RNA sequences that encode the above beneficial proteins are also contemplated.

In another embodiment, the invention contemplates the delivery of antisense or ribozyme nucleic acids to hair follicle cells for the purpose of selectively inhibiting hair follicle gene expression, and control aspects of hair follicle cell function.

Antisense nucleic acids are generally well known in the art and function to hybridize with sense strands of messenger RNA (mRNA), thereby interfering with the normal expression of the hybridized mRNA molecule. The sequence of the antisense nucleic acid depends, as is well known, upon the nucleotide sequence of the mRNA to be hybridized. See for example, Stein et al., *Science*, 261:1004–1012)1993).

Ribozyme nucleic acids are also generally well known in the art as single-stranded (ss) RNA molecules that are capable of selectively cleaving ssRNA and ssDNA. The ribozyme is useful to selectively inhibit gene expression by cleavage of a target ssRNA or ssDNA molecule in a hair follicle cell.

Representative targets for antisense or ribozyme nucleic acids are deleterious genes in hair follicle cells, such as the genes responsible for baldness, hair loss, loss of hair color, strength or condition, and the like undesirable features of hair follicles and hair shafts. In a preferred embodiment, the invention contemplates liposome-mediated delivery of an antisense or ribozyme nucleic acid capable of inhibiting expression of the gene that produces androgen receptor, thereby inhibiting follicle cell production of the receptor, thereby reducing hair loss.

The preparation and use of antisense or ribozyme nucleic acids is well known in the art, and the design of particular antisense or ribozyme nucleic acids are not themselves considered to be part of the present invention. However, insofar as the invention contemplates methods for liposome-mediated delivery of antisense or ribozyme nucleic acids to hair follicles for the purpose of improving delivery and selectivity of the effect exerted by the delivered nucleic acid, the present invention is not to be limited to any particular species thereof but rather describes general methods of their delivery as a beneficial compound.

DNA segments (i.e., synthetic oligonucleotides) used to produce a larger DNA segment that encodes a beneficial protein can easily be synthesized by chemical techniques, for example, the phosphotriester method of Matteucci, et al., (*J. Am. Chem. Soc.*, 103:3185–3191, 1981) or using automated synthesis methods. In addition, larger DNA segments can readily be prepared from smaller DNa segments by well known methods, such as synthesis of a group of oligonucleotides that define the DNA segment, followed by hybridization and ligation of oligonucleotides to build the complete segment.

Furthermore, DNA segments consisting essentially of structural genes encoding a beneficial protein can be obtained from recombinant DNA molecules containing a gene that defines the beneficial protein isolated from natural sources. Exemplary natural sources are described in the references cited herein where the cDNA sequences are described.

In addition, the invention contemplates the use of a recombinant DNA molecule (rDNA) containing a DNA segment of this invention. A rDNA can be produced by operatively linking a vector to a DNA segment of the present invention.

As used herein, the term "vector" refers to a DNA molecule capable of autonomous replication in a cell and to which another DNA segment can be operatively linked so as to bring about replication of the attached segment. A vector capable of directing the expression of a gene that encodes a beneficial protein is referred to herein as an "expression vector". Thus, a recombinant DNA molecule is a hybrid DNA molecule comprising at least two nucleotide sequences not normally found together in nature.

The choice of vector to which a DNA segment of the present invention is operatively linked depends directly, as is well known in the art, on the functional properties desired, e.g., protein expression, and the host cell to be transformed, these being limitations inherent in the art of constructing recombinant DNA molecules. However, a vector contemplated by the present invention is at least capable of directing the replication, and preferably also expression, of the beneficial protein structural gene included in DNA segments to which it is operatively linked.

In preferred embodiments, a vector contemplated by the present invention includes a procaryotic replicon, i.e., a DNA sequence having the ability to direct autonomous replication and maintenance of the recombinant DNA molecule extrachromosomally in a procaryotic host cell, such as a bacterial host cell, transformed therewith. Such replicons are well known in the art. In addition, those embodiments that include a procaryotic replicon also include a gene whose expression confers drug resistance to a bacterial host transformed therewith. Typical bacterial drug resistance genes are those that confer resistance to ampicillin or tetracycline.

Those vectors that include a procaryotic replicon can also include a procaryotic promoter capable of directing the expression (transcription and translation) of the beneficial protein gene in a bacterial host cell, such as *E. coli*, transformed therewith. A promoter is an expression control element formed by a DNA sequence that permits binding of RNA polymerase and transcription to occur. Promoter sequences compatible with bacterial hosts are typically provided in plasmid vectors containing convenient restriction sites for insertion of a DNA segment of the present invention. Typical of such vector plasmid are pUC8, pUC9, pBR322 and pBR329 available from Biorad Laboratories, (Richmond, Calif.) and pPL and pKK223 available from Pharmacia, Piscataway, N.J.

Expression vectors compatible with eucaryotic cells, preferably those compatible with mammalian cells, and particularly hair follicle cells, can also be used to form the recombinant DNA molecules for use in the present invention. Mammalian cell expression vectors are well known in the art and are available from several commercial sources. Typically, such vectors are provided containing convenient restriction sites for insertion of the desired DNA segment, and provide the signals required for gene expression in a mammalian cell. Typical of such vectors are the pREP series vectors and pEBVhis available from Invitrogen (San Diego, Calif.), the vectors pTDT1 (ATCC #31255), pCP1 (ATCC #37351) and pJ4W (ATCC #37720) available from the American Type Culture Collection (ATCC) and the like mammalian expression vectors.

Particularly preferred are mammalian expression vectors which allow the expression of the gene in a tissue-specific manner, in this case by the action of a regulatory promotor that will limit gene expression to hair follicle cells.

Successfully transformed hair follicle cells, i.e., follicle cells that contain a rDNA molecule of the present invention, can be identified by well known techniques. For example, cells resulting from the introduction of an rDNA of the present invention can be subjected to assays for detecting the presence of specific rDNA using a nucleic acid hybridization method such as that described by Southern, *J. Mol. Biol.*, 98:503 (1975) or Berent et al., *Biotech.*, 3:208 (1985).

In addition to directly assaying for the presence of rDNA, successful transformation can be confirmed by well known immunological methods for the presence of expressed protein. For example, follicle cells successfully transformed with an expression vector produce proteins displaying beneficial protein, which then can be assayed directly by immunological methods.

Alternatively, successful transformation of the target tissue can be confirmed by evaluation of the target tissue for indicia of function exerted by the administered beneficial compound. For example, where the compound is a nucleic acid expressing tyrosinase, as described in the Examples, the exerted function of pigmentation, or the presence of tyrosinase activity or enzymatic conversion of L-dopa to product can be detected directly in the target tissue.

B. Methods for Identifying Genes That Encode Proteins Beneficial to Hair Follicles In another embodiment, the invention provides a method for identifying a gene that encodes a protein that can exhibit a beneficial effect upon a hair follicle. The method comprises the steps of (1) encapsulating a nucleic acid molecule containing the gene of interest into a liposome composition of this invention, (2) contacting the nucleic acid-containing (encapsulated) liposome with a skin sample histoculture as described herein and having at least one hair follicle, thereby delivering the nucleic acid to the follicle, and (3) observing whether the delivered nucleic acid, upon expression of any protein encoded thereon, exhibits a beneficial effect on the hair follicle. The effect observed can be changes in hair color, condition, growth rate, viability, condition of the associated hair follicle cell structures, and the like indicia of cellular response.

In one embodiment, the present method is well suited to screening gene libraries for the presence of a gene capable of expressing a protein that exhibits a beneficial effect on a hair follicle. Gene libraries can be in the form of cDNA libraries or genomic DNA libraries as is well known. The beneficial effect to be induced depends on the screening method to detect the effect, as described further herein.

The following Examples serve to illustrate particular embodiments of the invention and are not limiting of the specification and claims in any way. The examples detail the application and testing of liposome-based treatments hair follicles and hair growth problems. Parts and percentages are by weight unless otherwise indicated.

EXAMPLE

1. Liposome-Mediated Delivery of Dye to Hair Follicles

Liposome-mediated delivery of beneficial agents to hair follicles is demonstrated using a native-state skin sample histoculturing method in which hair follicle-containing skin samples are cultured allowing the growth of the hair follicle, and detailed observation of the hair follicle cells during the treatment with therapeutic liposomes.

For the histoculture of skin, pieces of shaved outbred white-haired-mouse or nude-mouse skin, approximately 2×5×2 mm, were harvested under a dissection microscope and then histocultured on collagen-gel supported sponge as described by Li et al., *Proc. Natl. Acad. Sci. USA*, 88:1908–1912, (1991). Histoculture was continued for about 24 hours prior to contacting the skin histoculture with the liposome preparation.

Liposomes were prepared by sonication of about 15 mg phosphatidylcholine (PC) emulsion in phosphate buffered saline (PBS) containing about 20 mg/ml of the fluorescent dye calcein. Liposomes were also prepared by entrapping NBD-phosphatidylcholine fluorescent dye using an emulsion with about 20 mg/ml of the NBD formulation. Liposomes were separated from the non-entrapped dye by gel-filtration on a Sepharose 4B column diluted with phosphate buffered saline. The amount of entrapped dye was measured spectrofluorometrically. Two types of PC were used: egg PC (EPC) and dipalmitoyl PC (DPPC). Due to their phase transition temperatures, liposomes made of DPPC are in a gel phase at about 37° C while liposomes prepared from EPC are in a liquid-crystalline state.

Samples of the mouse skin histocultures were incubated for about 20 minutes with each of the liposomes and with a solution of "free" calcein dye at the same concentrations used in the liposome preparation. After the tissue samples were thoroughly washed with culture medium free of liposomes to remove excess liposome composition, the specimens were analyzed with a BioRad MRC 600 laser confocal microscope with a BHS filter block, which excites the tissue at 488 nm and passes the light emitted at 520 nm. These parameters are close to the excitation and emission maxima reported for calcein, Haugland,(Ed.) *Molecular probes. Handbook of Fluorescent Probes and Research Chemicals*, Molecular Probes, Inc., Eugene, (1989–1991 and 1992–1993). There is no autofluorescence of tissue when these emission and excitation wavelengths are used. The MRC-600 Confocal Imaging System (Bio-Rad, Richmond, Calif.) was mounted on a Nikon Optiphot equipped with a 10× PlanApo Objective.

Figure 1B:
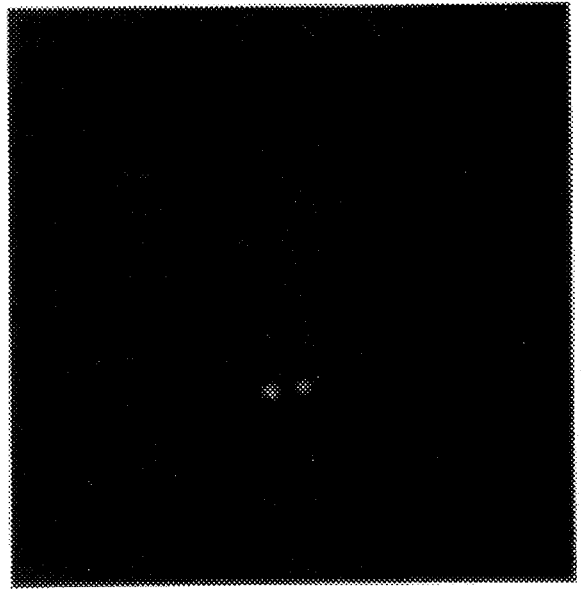
FIG. 1B is a fluorescent microscopy image (magnification 500×) of a skin histoculture treated with calcein without liposomes as described in Example 1, showing weak dye staining and no preferential delivery to skin structures.

FIG. 1A shows the skin histoculture incubated with calcein-entrapped EPC liposomes. Note the high efficiency of the delivery of the fluorescent dye preferentially into hair follicles. FIG. 1B shows the skin histoculture incubated with free calcein solution. Note the relatively low fluorescence with no preferential staining of any particular skin structure. The image in FIG. 1B was made with the same parameters of aperture and gain control as FIG. 1A.

To study the differences in liposome-mediated delivery depending upon the type of liposome used, additional liposomes were prepared as above except using DPPC in the liposome. The results obtained using either calcein or NBD-phosphatidylethanolamine as the fluorescent label showed selective labelling of the hair follicle at the surface of the follicle rather than inside the follicles when EPC was used. Thus, different liposome compositions allow even greater selectivity in delivery to a preselected region of the follicle.

The above results show a difference between substantially preferential staining of hair follicles obtained with dye entrained in DPPC or EPC liposomes compared to a lack of preferential staining of follicles over skin with free dye. Thus, liposome-entrapped dye, in contrast to free dye, becomes specifically associated with hair follicles, indicating that liposomes specifically target hair follicles.

2. Liposome-Mediated Delivery of Melanin to Hair Follicles

The targeted delivery of a beneficial compound to hair follicles was demonstrated using melanin as the model because melanin provides the benefit of pigmentation.

To that end, liposomes were prepared by sonication. About 20 mg of egg phosphatidycholine was rotary evaporated with a vacuum drier from a chloroform solution to form a thin film on the walls of a 5 ml round-bottomed flask for about 1 hour. The dried thin film phospholipid was suspended in about 0.5 ml phosphate buffered saline (pH 7.4) on a vortex mixer and then sonicated with a Branson probe-type sonicator fitted with a microtip at power level 3 for about 8 minutes. Then 0.5 ml of a solution of melanin (10 mg/ml) was entrapped with the above suspension by sonication for about an additional 4 minutes. Liposomes were separated from the non-entrapped melanin by gel-filtration on a Sepharose 4B column equilibrated with phosphate buffered saline.

Pieces of outbred white-haired mouse skin derived from 1–2 weeks-old animals (about 2×5×2 mm each) were harvested under a dissection microscope. The samples were then histocultured on collagen-gel supported sponges as described in Example 1. Liposome interaction with the skin was initiated after about 24 hours of histoculture. Mouse skin histocultures were incubated for about 12 hours with liposomes. As a control, a solution of "free" melanin at the same concentration as was used in the liposome preparation was also incubated for about 12 hours with pieces of the histocultured skin.

The skin histocultures were counter-stained with the dye 2',7'-bis(2-carboxyethyl)-5 which is activated to fluorescence by nonspecific esterases present only in living cells. After the tissues were thoroughly washed, the specimens were analyzed with a Nikon fluorescence microscope equipped with a fluorescein cube. Microscopically the live tissues and cells fluoresced green such that dark dense melanin deposits localized in the tissue can be clearly identified against the green background. All skin samples were then fixed with formalin and processed through dehydration, paraffinization, paraffin-embedding and hematoxylin and eoxin (H&E) staining.

Figure 2:
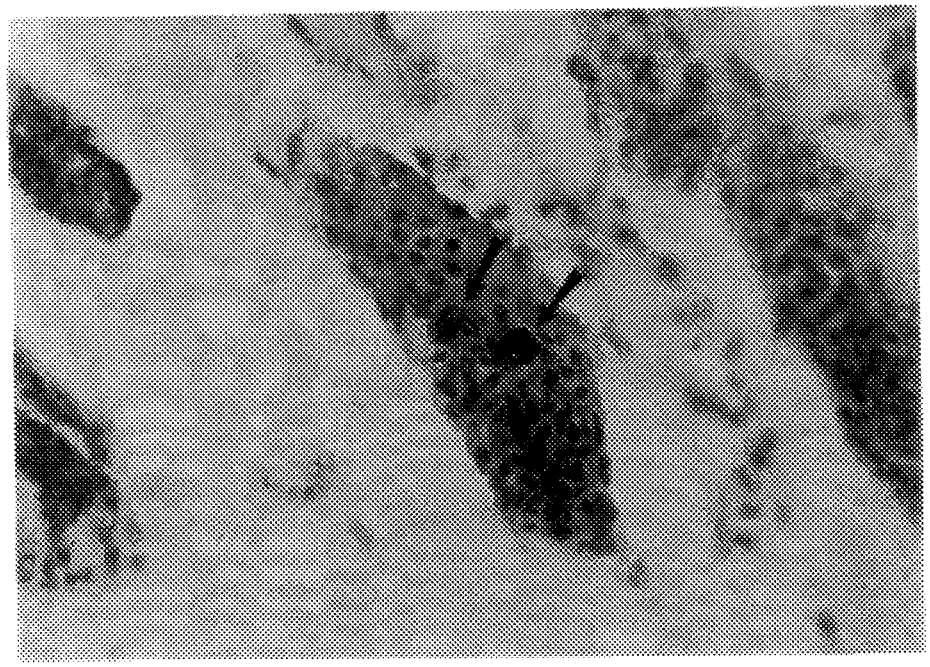
FIG. 2 is a hematoxylin and eosin stained paraffin-section of white-haired mouse skin treated with melanin entrapped liposomes for 12 hours, (magnification 500×) as described in Example 2, showing that the liposome-entrapped melanin primarily delivered the melanin to hair follicles as indicated by the arrows.
Figure 3:
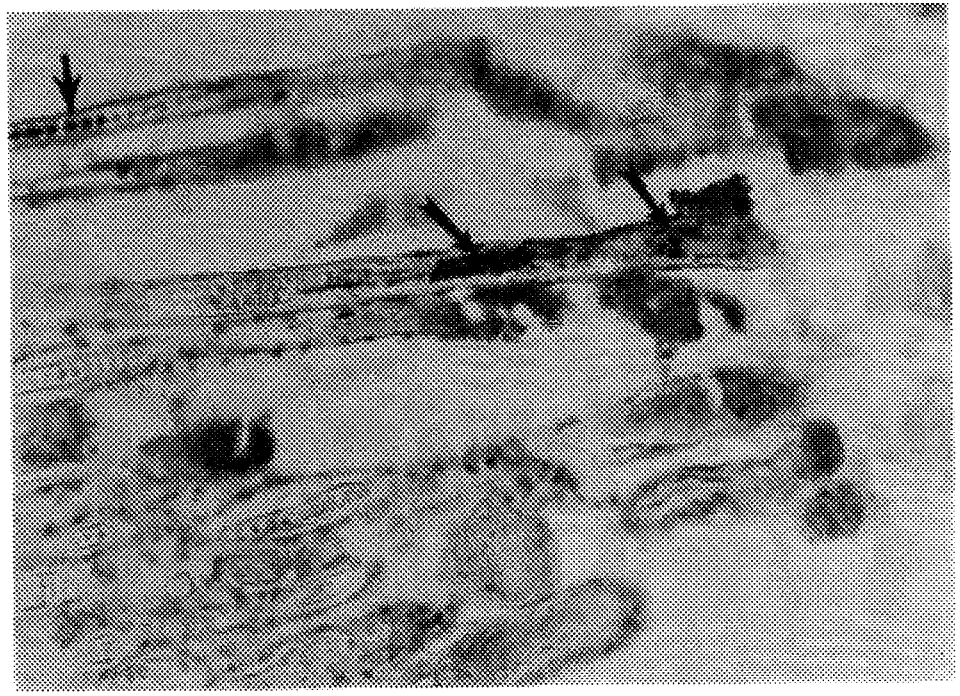
FIG. 3 is a light microscopy image (magnification 250×) of a paraffin section of skin histoculture as in FIG. 2 stained with hematoxylin and eosin as described in Example 2, showing delivery of melanin into the hair shaft itself as indicated by the arrows.

FIG. 2 shows the liposome-mediated targeted delivery of melanin to the hair follicles in the skin histocultures stained with H&E. In the paraffin section of white-haired mouse skin treated for 12 hours with the melanin-entrapped liposomes, the majority of the melanin can be seen to be localized around the hair follicles. The melanin can be seen at the periphery of follicles and in the follicle cells themselves. FIG. 3 shows a side view of a H&E-stained hair follicles, showing that the liposome-entrapped melanin was delivered into the hair shaft itself to form the band-like melanin-distribution pattern in the terminally-differentiated keratinocytes of the typical normal pigmented hair shaft. Note that the liposome-delivered melanin seen in FIG. 3 exhibits a natural pattern in the hair shaft mimicking a natural melanized hair shaft. In the control (not shown), in which the skin histocultures had been incubated with the "free" melanin, no "free" melanin can be observed either in hair shafts or the hair follicular cells.

Thus, liposomes can specifically target an important, large, polymer to hair follicles and even enter into the hair shaft itself in a normal pattern.

3. Liposome-Mediated Delivery of Nucleic Acid to Hair Follicles a. Delivery of Nucleic Acids to a Cultured Cell Line The targeted delivery of nucleic acid to hair follicles was demonstrated using mouse genomic DNA cleaved to about 1 kilobase (kb) lengths as the model for nucleic acids capable of expressing protein due to the typical size of a DNA expression vector, and the size of a typical structural gene.

About 1 kb DNA was isolated from a mouse genomic DNA library and purified from low melting point agarose with the Magic DNA Purification Kit (Promega, Madison, Wis.). About 50 ng DNA was labeled with [$^{35}$S]dATP (DuPont) with the Random Primer DNA Labeling Kit (BioRad, Richmond, Calif.). The specific activity of the labeled DNA with $^{35}$S-dATP was $2.6 \times 10^{10}$ cpm/µg.

Liposomes were prepared by freezing and thawing. About 20 mg of egg phosphatidylcholine (EPC) was rotary evaporated with a vacuum drier from a chloroform solution to form a thin film on the walls of a 5 ml round-bottomed flask for about 1 hour. The dried film phospholipid was suspended in an about 0.5 ml phosphate buffered saline solution at a pH of about 7.4 in a vortex mixer and then sonicated with a Branson probe-type sonicator fitted with a microtip at power level 3 for about 8 minutes. The 0.5 ml of [$^{35}$S]dATP-labeled DNA solution was added to the above suspension by extensive vortexing for about 1 minute and followed by freezing and thawing. Liposomes were separated from the non-entrapped [$^{35}$S]dATP by gel-filtration on a Sepharose 4B column equilibrated with PBS. About 50 µl calcein (about 10 mg/ml) was added into the solution in order to mark the liposomes during the separation. The specific activity of the entrapped DNA labeled [$^{35}$S]dATP was $2.5 \times 10^{10}$ cpm/µl measured by liquid scintillation counting.

Pieces of outbred white-haired-mouse skin (about 1×5×2 mm) derived from 1–5 week-old animals were harvested under a dissection microscope and then histocultured on collagen-gel-supported sponges as described in Example 1. Liposome interaction with the skin was initiated after about 24 hours of histoculture. Mouse skin histocultures were then incubated for about 44 hours with liposomes. As a control, a solution of naked-[35S]DNA at the same concentration was used in the liposome preparation and was also incubated with skin histocultures.

The skin histocultures were washed with phosphate-buffered saline, pH 7.0, placed in histology capsules and fixed in 10% (v/v) formalin. The fixed skin cultures were then dehydrated, embedded in paraffin, sectioned and placed on slides by standard methods well known to those of skill in the histology art. The slides were deparaffinized, coated with Kodak NTB-2 emulsion, exposed for 5 days and developed. See, e.g. Freeman et al., *Proc. Soc. Natl. Acad. Sci. USA*, 83:2694–2698 (1986) Hoffman et al., *Proc. Soc. Acad. Sci. USA*, 86:2013–2017 (1989); and Li et al., *Proc. Soc. Acad. Sci. USA*, 88:1908–1912 (1991). The developed slides were rinsed, stained with hematoxylin and eosin and examined using a Nikon or Olympus photomicroscope fitted with epi-illumination polarization.

Figure 4:
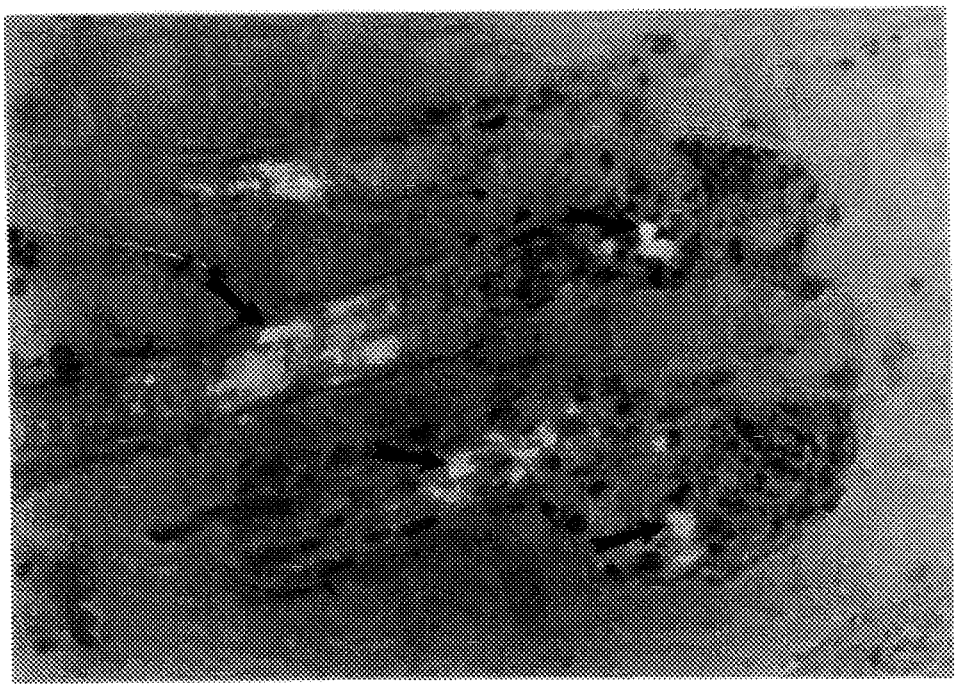
FIG. 4 is a histological autoradiogram of histocultured skin treated with liposomes entrapped with radioactive labeled high-molecular weight DNA showing the localization of DNA (arrows) in hair follicle cell membrane and cytoplasm, as described in Example 3.
Figure 5A:
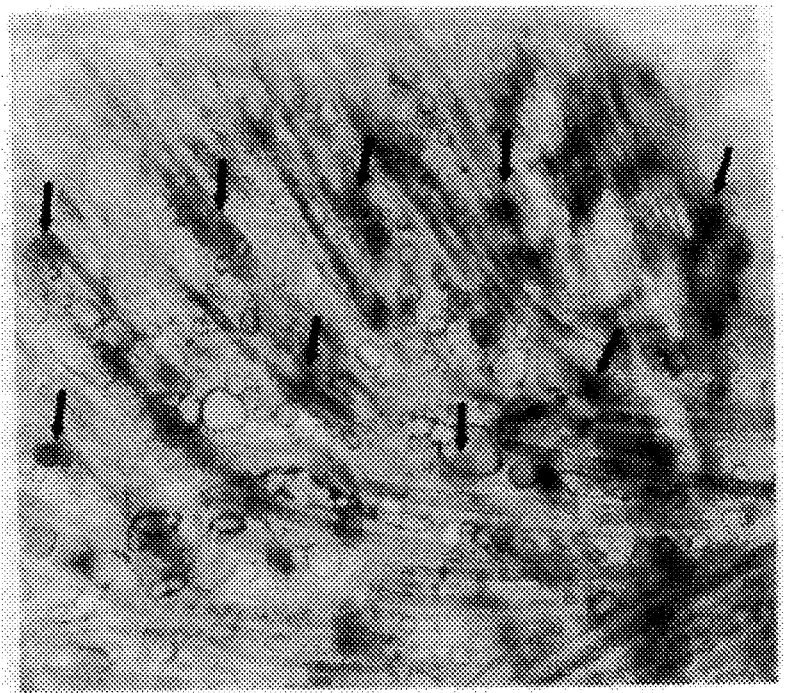
Figure 5B:
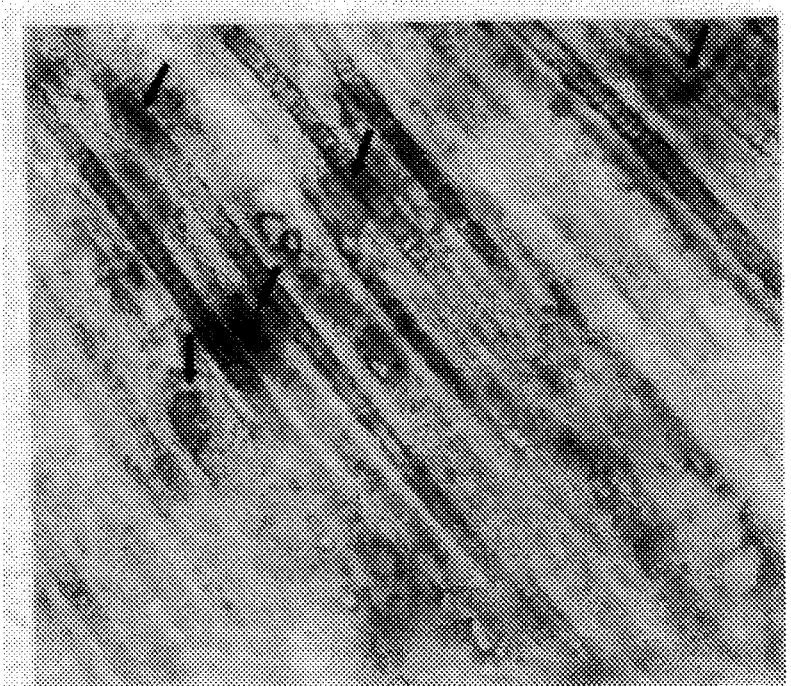
Figure 5C:
Figure 5D:
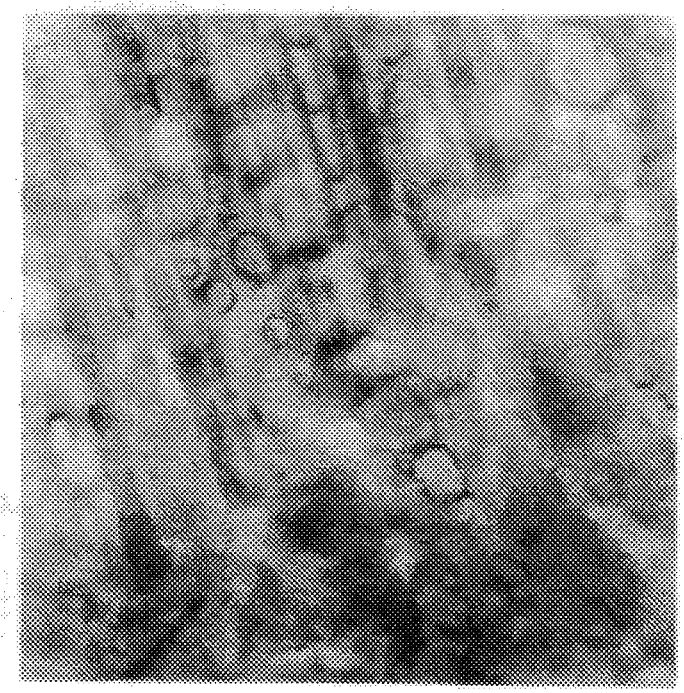

The histological autoradiogram of FIG. 4 shows [$^{35}$S] DNA-labeled hair and follicle cells in the histocultured skin after the skin was incubated with the DNA liposomes for about 44 hours. High radioactive labeling by the [$^{35}$S]DNA in the cell membranes and cell cytoplasm as well as in the cell nucleus can be seen in FIG. 4, as pointed out by the arrows. This shows that the liposomes have delivered the DNA across the cell membrane and the DNA is transported through the cytoplasm to the nucleus.

When the histocultured skin was treated with naked-[$^{35}$S] DNA there were only a few radioactive labelled cells. For further comparison, the percent of labeled follicles per 20× field and percent of labeled cells per follicle in the areas of maximum labeling can be calculated from the autoradiogram of FIG. 4. The percent of labeled follicles per 20× field is found to be about 7 times higher for the liposome carried labeled DNA compared to the naked labeled DNA, and the percent of labeled cells per follicle is at least 4 times higher for the liposome carried labeled DNA compared to the naked labeled DNA.

This Example demonstrates that liposomes can specifically and efficiently target DNA into the hair follicles, and therefore establish that liposome encapsulated nucleic acids are useful reagents for targeting gene therapy to hair growth processes.

b. Delivery of Liposome-Entrapped Nucleic Acid Expressing the Human Tyrosinase Gene to a Cultured Cell Line Cloned human tyrosinase gene was transferred to tissue cultured cell lines using liposomes to demonstrate the efficiency of liposome-mediated delivery and expression of a tyrosinase gene.

To that end, liposomes were prepared by well known freezing and thawing methods. About 20 mg of phospholipid in a ratio of 5:3:2 of phosphatidylcholine (PC): cholesterol (Chol): phosphatidylethanolamine (PE) was rotary evaporated with a vacuum drier from a chloroform solution for 1 hour to form a thin film on the walls of a 5 ml round-bottomed flask for about 1 hour. The dried film phospholipid was suspended in 2 ml phosphate buffered saline solution at a pH of about 7.4 (PBS) in a vortex mixer and then sonicated with a Branson probe-type sonicator fitted with a microtip at power level 3 for about 8 minutes. Then 200 ug of the plasmid pRHOHT2 was entrapped in a liposome by addition of the plasmid to the sonicated suspension, sonication of the admixture in a water bath for 2 minutes, followed by freezing and thawing three times to form nucleic acid-containing liposome composition.

Plasmid pRHOHT2 was obtained from Dr. S. Shibahara and is described by Shibahara et al., *J. Biol. Chem.*, 262:12889–12892 (1987), and Takeda et al., *Biochem. Biophys. Res. Comm.*, 162:984–990 (1989), and contains a full length human tyrosinase cDNA, including promoters for expression of tyrosinase in mammalian cells.

Human fibroblast FS-3 and mouse amelanotic K1735 cell lines were each pre-cultured in 60 mm culture dishes with Eagle's MEM medium containing 10% fetal bovine serum (FBS) and Dulbecco's Modified Eagle's medium containing 10 FBS, respectively, for 24 hours. Thereafter, the cultured cells were contacted with 0.5 ml of the tyrosinase gene-entrapped liposome composition in 1.5 ml of the respective culture medium per culture dish, and the contacted cells were maintained for 48 hours under culturing conditions. Thereafter, the cells were further cultured for 7 days (FS-3) or 3 days (K1735) with normal culture medium after aspiration of the liposome-containing medium. The cells were then harvested by trypsin digestion and centrifuged at 800× g for 5 minutes to attach the cells to cytospin slides. As a control, 50 micrograms (ug) of naked plasmid in 0.5 ml medium was added to the two cell types in place of the 0.5 ml liposome preparation.

The expression of tyrosinase was evaluated by measuring dopa-oxidase reactions and immunhistochemical staining for tyrosinase in the treated cells.

To detect dopa oxidase activity, the cytospin slides were incubated with 1 mg/ml of L-dopa in PBS for 12 hours at 37 degrees C. as described by Kugelman et al., *J. Invest. Dermatol.*, 37:73–76 (1961). Thereafter, the cytospin slides were counterstained with hematoxylin and eosin by established procedures, and the dopa oxidase-positive cells were identified and counted using a microscope.

To detect tyrosinase immunohistochemically, a Dako LSAB (labeled streptavidin-biotin) kit was used to stain tyrosinase-containing cells. The cytospin slides were fixed in acetone for 10 minutes, and then air-dried. Thereafter, serial incubations were then performed for 10 min each sequentially in hydrogen peroxide, blocking serum, a dilution (1:400) of primary antibody (anti-tyrosinase), linking antibody, peroxidase-conjugated streptavidin, and 3-amino-9-ehtylcarbazol substrate solution as described by the manufacturer of the kit (Dako, Carpinteria, Calif.). The primary antibody was rat anti-human tyrosinase monoclonal antibody TMH1 described by Tomita et al., *J. Invest. Dermatol.*, 85:426–430 (1985), and Jimenez et al., *Proc. Natl. Acad. Sci. USA*, 85:3830–3834 (1988). The linking antibody was a mixture of anti mouse and anti rat IgG conjugated to biotin, provided by the manufacturer (Dako). The treated cytospin slides were then lightly counterstained with Mayer's hematoxylin and mounted with liquid glycerol gelatin (Dako). A positive control was similarly prepared using a frozen section of human melanoma tissue. A negative control was prepared by replacing the primary antibody with PBS.

The results show tyrosinase expression in both FS-3 and K1735 liposome-treated cells, when detected by either dopa oxidase reaction of by immunohistochemical staining. The percent of cells expressing tyrosinase was approximately 52% of the total cells, by either assay method. The negative control cells were negative for both the oxidase assay and the immunohistochemical staining assay.

When compared to the calcium phosphate method for transfection of nucleic acid into cultured cells, it was observed that efficiency of transfer of a tyrosinase-gene expression plasmid into cells was about 50 times greater when liposomes were used in comparison to calcium phosphate.

These results demonstrate that liposomes are effective and efficient at delivering nucleic acid expression vectors into cells, and further that the liposomes can deliver expression vector plasmid which are subsequently able to express the encoded gene. Finally, the results demonstrate that the tyrosinase gene can be effectively introduced and expressed in mammalian cells.

c. Delivery and Expression of Beta-Galactosidase Gene in Hair Follicles of Histocultured Skin The bacterial gene lac-Z encoding beta-galactosidase was delivered to histocultured skin samples in a liposome preparation to demonstrate selective delivery and expression in hair follicles. Plasmid pM-MuLV-SV-Lac-Z contains a mammalian promoter derived from the Moloney murine leukemia virus (M-MuLV) and the SV40 Virus (SV) which controls the expression of the beta-galactosidase gene (Lac-Z) capable of expression of beta-galactosidase in mammalian cells.

Liposomes were prepared as described in Example 3b, except that the phospholipids comprised PC, PE and cholesterol in a ratio of 5:2:3, and the ratio of plasmid DNA to phospholipid was 200 ug DNA per 20 mg total phospholipid.

White-haired mouse skin was histocultured as described in Example 1, except that the liposome composition was maintained in the culture medium for four days. Thereafter, the skin histoculture medium was changed to the same medium lacking liposomes and including the Lac-Z substrate X-gal, and the X-gal-containing medium was maintained under histoculturing conditions for 18 hours to allow any beta-galactosidase present in the histocultured skin sample to convert the X-gal to the typical visible blue dye. Control liposome delivery was conducted with naked plasmid DNA (pM-MuLV-SV-Lac-Z) using the same amount of DNA as with the liposome-entrapped plasmid composition.

Histocultured skin samples were then sectioned for histochemistry and evaluated using light microscopy at 125× and 250× magnification. The results are shown in FIGS. 5A–5D. The presence of expressed Lac-Z gene indicated by dark blue spots is only seen in FIGS. 5A and 5B which received liposome-entrapped plasmid; no dark spots are observed in FIGS. 5C and 5D. Furthermore, the dark spots are observed in the hair follicles and not significantly observable in the tissues adjacent to the hair follicles.

The results show that the Lac-Z gene was expressed in hair follicles and was not detectable in the other portions of the histocultured skin sample, indicating the selectivity of the liposome delivery method.

4. In Vivo Liposome-Mediated Delivery of Beneficial Compounds to Hair Follicles in Mice The present methods were used to deliver beneficial compounds to hair follicles in vivo by administration of a liposome composition of the present invention containing either melanin or calcein to mice.

Liposomes were prepared essentially as described in Example 1. Twenty milligram (mg) of PC were rotary evaporated as described, and resuspended by sonication in 0.5 ml of PBS. Thereafter, 0.5 ml of either calcein (10 mg/ml) or melanin (10 mg/ml) solution, respectively, were added to sonicated PC liposome composition, and further sonicated for 6 minutes, followed by freeze-thawing three times. The resulting liposome composition was extruded through a 0.6–1.0 uM filter and separated from the nonentrapped calcein or melanin by gel filtration on a Sepharose 4B column eluted with PBS to form liposome-entrapped beneficial compound composition (calcein or melanin).

Two to 4 week-old pre-shaved outbred white-haired mice were used for in vivo topical liposome delivery of entrapped beneficial compound to hair follicles. A sample of about 250 microliters of the liposome composition entrapping calcein or melanin was applied directly to the dorsal skin on the mouse in an area of approximately 1.5 $cm^2$ using a sutured bandaid patch to immobilize the liposome composition onto the skin and to prevent evaporation. The liposome composition was re-applied every 1 hour for 6 hours, with the last application remaining for a total of 24 hours at which time the skin samples were taken by punch biopsy for analysis. For time course experiments, one mouse was used for each time period, with 6 punch biopsies taken from each mouse, at 0.5, 1, 2, 4, 6, 16 and 24 hours. Prior to punch biopsy, the skin was cleaned with an alcohol swab to eliminate any material remaining on the surface of the mouse's skin. For controls, the same amount of calcein or melanin was applied without liposome as with samples containing liposome-entrapped beneficial compound.

After liposome treatment, the skin samples were harvested and cut to very thin (5 mm) pieces of tissue sectioned along the vertical direction of the hair follicles, and subsequently observed by either light or fluorescent microscopy and photographed. For melanin-treated samples, the tissue sample was first counter-stained with BCECF-AM and propidium iodide (PI) for fluorescent microscopy, or prepared for histology and stained in paraffin sections using hematoxylin and eosin for light microscopy. For calcein-treated samples, the tissue sample was first counter-stained with propidium iodide (PI) for fluorescent microscopy.

Skin samples containing calcein were also analyzed by spectrofluorimetry to determine the effective concentration of a delivered beneficial compound into a selected tissue. To that end, three samples each containing two pieces of a 2-mm punch biopsy of skin for each time point were put into 2 ml of PBS and sonicated in the water bath sonicator for 2 min. The sonicated sample was then centrifuged for 10 minutes in a microcentrifuge at 14,000× g, and the resulting supernatant was measured by spectrofluorimetry at an excitation wavelength of 496 nm and an emission wavelength of 517 nm for detecting calcein. The concentration of calcein delivered into the skin tissue was determined from the spectrofluorometric readings by comparison to a standard curve.

Figure 6A:
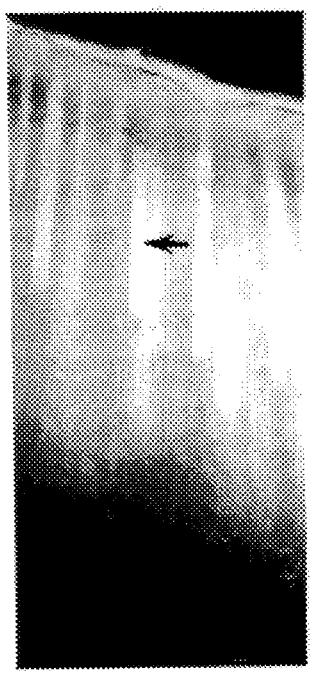
Figure 6B:
Figure 6C:

FIGS. 6A–6C show the results of delivery of calcein using liposome-entrapped calcein (FIGS. 6A and 6B) and naked calcein (FIG. 6C) after 20 hours. Notice that the liposome-mediated delivery has allowed the calcein to penetrate deep into the hair follicles and shafts, whereas control calcein was trapped in the stratum corneum and did not enter the hair shafts or follicles.

Time course analysis of effectiveness of liposome-entrapped calcein-mediated delivery showed that by 24 hours 22.15 nanograms (ng) per $mm^2$ of calcein was observed delivered in the hair follicles, whereas only about 1.4 ng/$mm^2$ of naked calcein was observed delivered after 24 hours, and this amount did not increase with time.

Figure 7A:
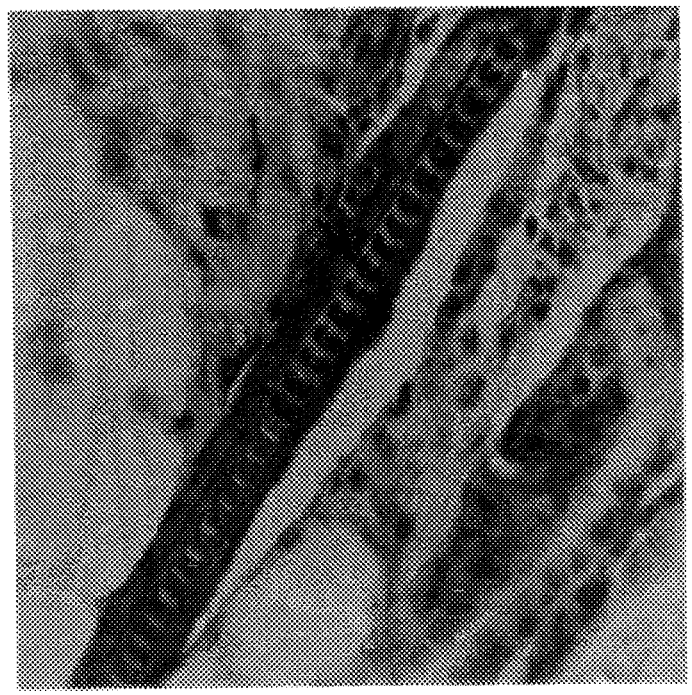
Figure 7B:
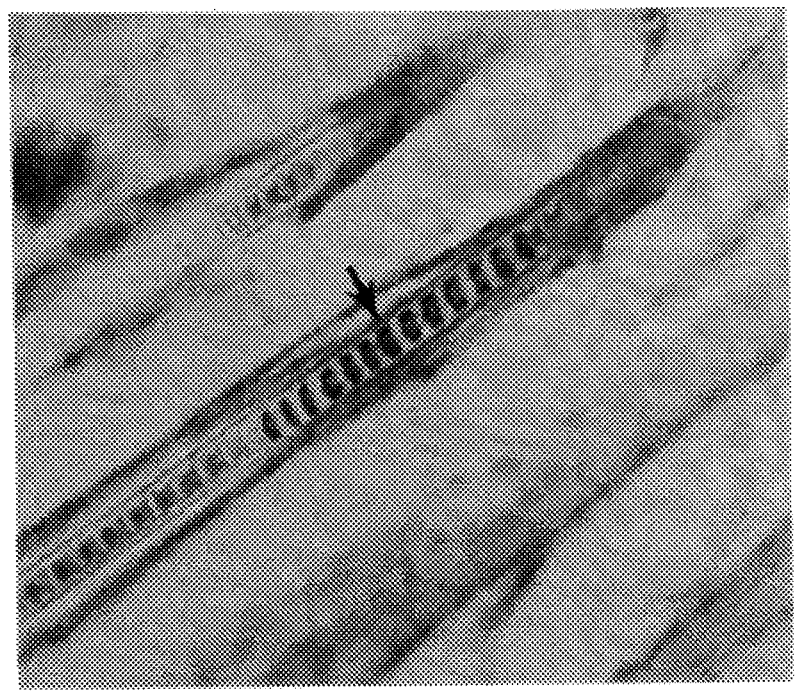
Figure 7C:
Figure 8A:
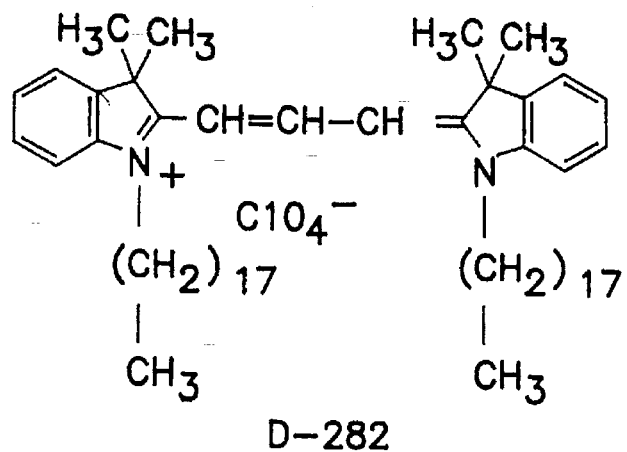
FIGS. 8A–8F shows the chemical structure of the cationic phospholipids D282, D378, D383, D3886, D3897 and D3899, respectively.
Figure 8B:
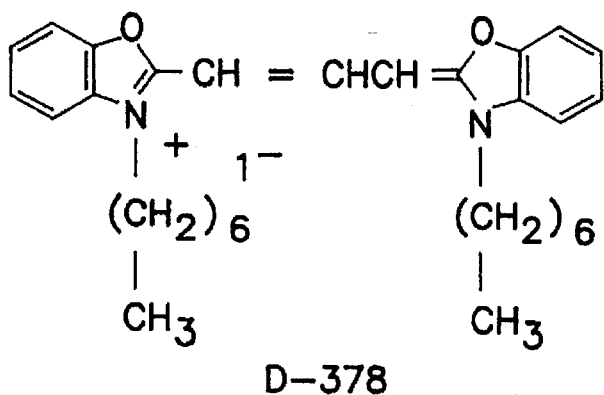
Figure 8C:
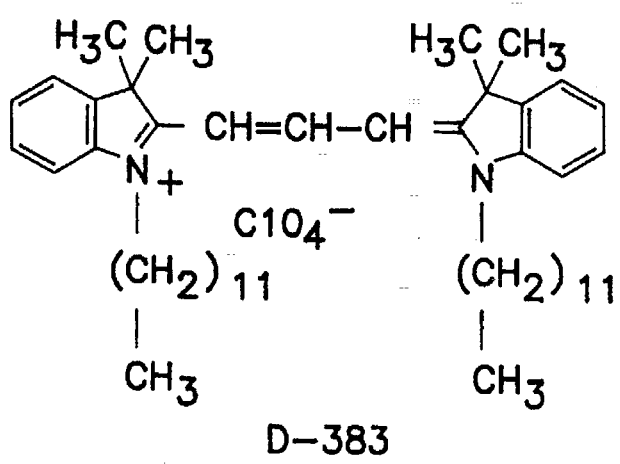
Figure 8D:
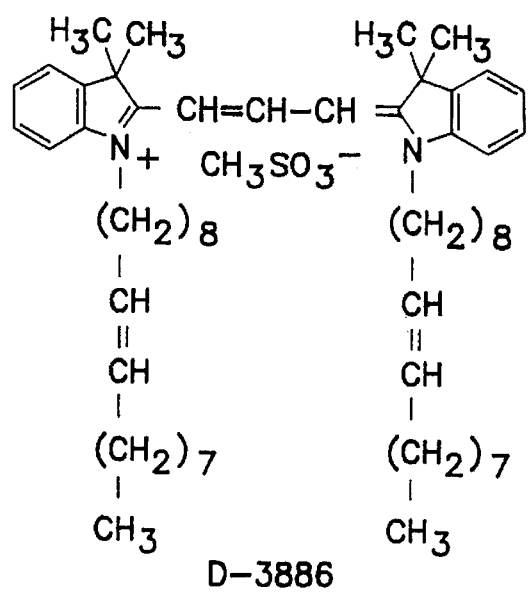
Figure 8E:
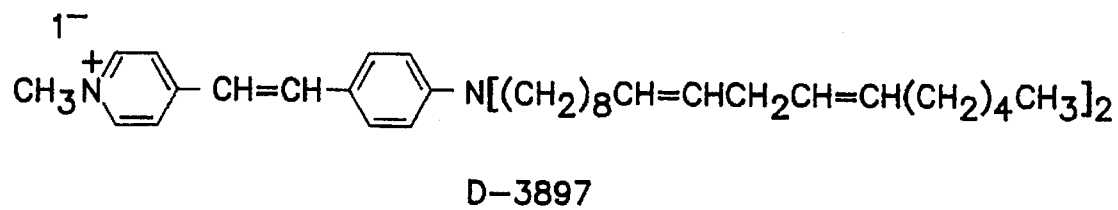
Figure 8F:
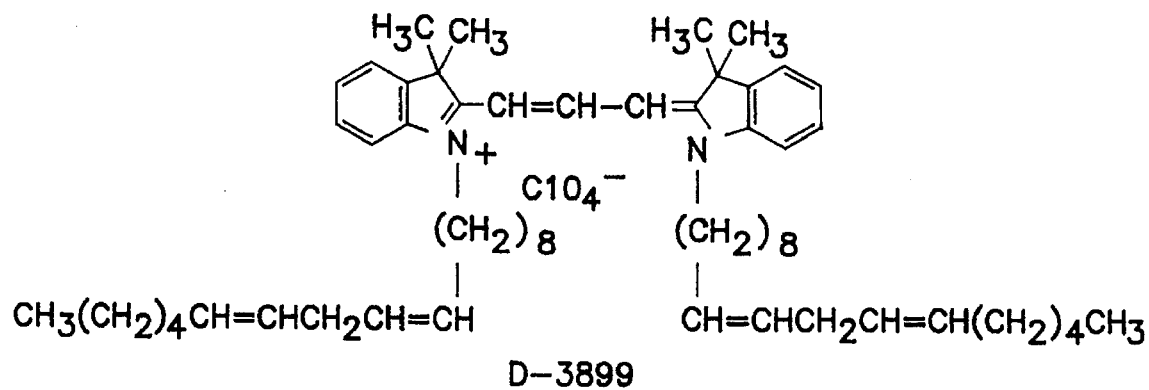

FIGS. 7A–7C illustrate the results in which melanin has been delivered using liposome-entrapped compound after 24 hours of treatment. FIGS. 7A and 7B show the melanin delivered into the hair shafts in a pattern that illustrates that the delivered melanin forms the exact pattern of naturally melanized hair shafts. FIG. 7C shows the melanin delivered into the hair follicle cells. Therefore, these results demonstrate that topical in vivo administration of liposome resulted in delivery of melanin to both the hair follicle and hair shaft.

Skin samples containing melanin were also analyzed by spectrophotometry to determine the effective concentration of a delivered beneficial compound into a selected tissue. To that end, three samples each containing two pieces of a 2-mm punch biopsy of skin for each time point were put into 2 ml of PBS and sonicated in the water bath sonicator for 2 min. The sonicated sample was then centrifuged for 10 minutes in a microcentrifuge at 14,000× g, and the resulting supernatant was measured by spectrophotometry at an absorption wavelength of 300 nm for detecting absorption by melanin. The concentration of melanin delivered into the skin tissue was determined from the spectrophotometric readings by comparison to a standard curve.

Readings from the skin samples in the time course study showed that liposome-entrapped melanin was delivered specifically to the hair follicles after 16 hours to a level of about 19.0 ug/mm$^2$ whereas less than 2.0 ug/mm$^2$ of melanin was delivered in the same time period using non-entrapped melanin.

The above results indicate that the liposome-targeted melanin or calcein were selectively delivered to the hair follicle and hair shafts within the follicle, but non-entrapped compound was not delivered to the hair follicle, and instead was restricted to the skin surface, particularly the stratum corneum. Therefore, the liposome-mediated delivery of beneficial compounds is seen to be effective at specific delivery to hair follicles and hair shafts in a living animal, demonstrating in vivo efficacy of the liposome-mediated delivery methods described herein.

As a further control plasma calcein concentrations were also measured by taking blood samples from the lateral tail vein of mice during the course of administration of liposome-entrapped calcein at 0.5, 1, 2, 4, 6, and 24 hours after topical administration. The harvested blood was transferred to a serum separator tube (Vacutainer, Becton Dickinson), and spun at 2000× g for 10 min to isolate plasma. Thereafter, calcein was measured by spectrofluorimetry at an excitation wavelength of 496 nm and an emission wavelength of 517 nm for detecting calcein. The concentration of calcein in the plasma was determined from the spectrofluorometric readings by comparison to a standard curve. Over a 24 hour time period, no detectable calcein entered the blood circulation. This is an important observation as it indicates that a beneficial compound, when administered by the present liposome-mediated methods, can be selectively targeted to the hair follicle and hair shaft without entry into the systemic circulation where it may exert undesirable side effects, and that safe follicle/shaft delivery is possible.

Although the present invention has now been described in terms of certain preferred embodiments, and exemplified with respect thereto, one skilled in the art will readily appreciate that various modifications, changes, omissions and substitutions may be made without departing from the spirit thereof.

---

What is claimed is:

1. A method of directly and selectively delivering melanin to hair follicles of a mammal comprising the steps of:
   a) providing a liposome composition consisting essentially of liposomes containing an effective amount of melanin; and
   b) applying said liposome composition topically to skin areas of a mammal having a plurality of hair follicles; whereby said melanin is preferentially transmitted to said hair follicles and enters into said hair follicles.

2. The method of claim 1 wherein said delivering occurs in vivo.

3. The method of claim 2 wherein said mammal is a human.

4. The method of claim 1 wherein said liposomes are pH-sensitive liposomes.

5. The method of claim 4 wherein said pH-sensitive liposomes are comprised of phosphatidylethanolamine and oleic acid in a molar ratio of 7:3.

6. The method of claim 1 wherein said liposomes are comprised of one or more phospholipids selected from the group consisting of phosphatidycholine, egg phosphatidylcholine, dioleoylphosphatidylcholine, dipalmitoylphosphatidylcholine, phosphatidylethanolamine, dioleoylphosphatidylethanolamine and cholesterol.

7. The method of claim 6 wherein said liposomes are comprised of phosphatidylcholine:phosphatidylethanolamine:cholesterol in a ratio of 5:2:3.

8. The method of claim 6 wherein said liposomes are further comprised of a cationic phospholipid selected from the group consisting of 1,1'-dioctadecyl-3,3,3',3'-tetramethylindocarbocyanine perchlorate, 3,3'-diheptyloxacarbocyanine iodide, 1,1'-didodecyl-3,3,3',3'-tetramethylindocarbocyanine perchlorate, 1,1'-dioleyl-3,3,3',3'-tetramethylindocarbocyanine methanesulfonate, N-4-(4-dilinoleylaminostyryl)-N-methylpyridinium iodide and 1,1-dilinoleyl-3,3,3'3'-tetramethylindocarbocyanine perchlorate.

9. The method of claim 8 wherein said liposomes contain a molar ratio of said one or more phospholipid to said cationic phospholipid of 0.8:1.0–1.2.

* * * * *